(12) United States Patent
Shimizu et al.

(10) Patent No.: US 8,102,266 B2
(45) Date of Patent: Jan. 24, 2012

(54) RADIO INTRA-SUBJECT INFORMATION ACQUIRING SYSTEM

(75) Inventors: Hatsuo Shimizu, Hachioji (JP); Takemitsu Honda, Hino (JP); Masayuki Hashimoto, Hachioji (JP); Kazutaka Nakatsuchi, Hino (JP)

(73) Assignee: Olympus Corporation, Tokyo (JP)

(*) Notice: Subject to any disclaimer, the term of this patent is extended or adjusted under 35 U.S.C. 154(b) by 1220 days.

(21) Appl. No.: 11/631,275

(22) PCT Filed: Jan. 21, 2005

(86) PCT No.: PCT/JP2005/000773
§ 371 (c)(1),
(2), (4) Date: Apr. 9, 2007

(87) PCT Pub. No.: WO2006/077643
PCT Pub. Date: Jul. 27, 2006

(65) Prior Publication Data
US 2008/0188712 A1    Aug. 7, 2008

(51) Int. Cl.
*H04Q 9/00* (2006.01)
*G08C 19/06* (2006.01)
*A61B 1/04* (2006.01)
*A61B 5/05* (2006.01)

(52) U.S. Cl. ............. 340/572.5; 340/572.1; 340/870.32; 600/118; 600/424

(58) Field of Classification Search ............... 340/572.1, 340/572.5, 10.1–10.4, 870.32; 600/118, 600/325, 327, 332, 424
See application file for complete search history.

(56) References Cited

U.S. PATENT DOCUMENTS

| | | | |
|---|---|---|---|
| 6,840,901 B2 * | 1/2005 | Onishi et al. | 600/118 |
| 7,881,668 B2 * | 2/2011 | Homan et al. | 455/41.3 |
| 2002/0165592 A1 | 11/2002 | Glukhovsky et al. | |
| 2010/0204566 A1 * | 8/2010 | Uchiyama et al. | 600/424 |

FOREIGN PATENT DOCUMENTS

| JP | 2001-231186 | 8/2001 |
|---|---|---|
| JP | 2004-328941 | 11/2004 |

* cited by examiner

*Primary Examiner* — Benjamin C Lee
*Assistant Examiner* — Omeed Alizada
(74) *Attorney, Agent, or Firm* — Scully, Scott, Murphy & Presser, P.C.

(57) ABSTRACT

A transmitting and receiving apparatus (2) that transmits a radio signal to a capsule endoscope includes: a transmitting level determining unit (25) disposed near a transmitting resonance circuit (22); a frequency controller (26) that controls an oscillation frequency based on a result of determination executed by the transmitting level determining unit (25); and a frequency variable oscillator (16) that changes the oscillation frequency, based on the control of the frequency controller (26). By changing the oscillation frequency so that a transmission level becomes large, the oscillation frequency can be changed so as to decrease a frequency difference between the oscillation frequency and the resonance frequency of the resonance circuit (22) that changes along a variation in a self inductance value of a coil (24).

10 Claims, 15 Drawing Sheets

20 # RADIO INTRA-SUBJECT INFORMATION ACQUIRING SYSTEM

TECHNICAL FIELD

The present invention relates to a radio intra-subject information acquiring system that includes a body-insertable apparatus that is inserted into the inside of a subject, and a transmitting and receiving apparatus that is disposed at the outside of the subject and performs radio communications with the body-insertable apparatus.

BACKGROUND ART

In recent years, a swallow-type capsule endoscope has appeared in the field of endoscope. The capsule endoscope has an imaging function and a radio communication function. After a patient swallows the capsule endoscope from the mouth for observation (examination), the capsule endoscope moves within the body cavity such as internal organs, for example a stomach and a small intestine following peristaltic motions thereof, and sequentially images, until the capsule endoscope is naturally discharged from the human body.

During a period while the capsule endoscope moves within the body cavity, image data picked up by the capsule endoscope inside the body is sequentially transmitted to the outside by radio communication, and is stored in a memory. The patient carries a receiver having the radio communication function and the memory function. With this arrangement, after the patient swallows the capsule endoscope, the patient can move freely, until the capsule endoscope is discharged. After the capsule endoscope is discharged, a doctor or a nurse can perform diagnosis by displaying the images of the organ on a display, based on the image data stored in the memory.

While the capsule endoscope can have such a configuration that driving power is supplied from an incorporated power source, a configuration which calls attention recently supplies driving power to the capsule endoscope from the outside via radio transmission. Based on the configuration in which the power is supplied from the outside, it is possible to avoid such a situation in which the driving of the capsule endoscope stops in the middle of the move in the body cavity due to an unintended exhaustion of power (see, for example, Patent Document 1).

FIG. 16 is a circuit diagram showing a configuration of a receiving antenna incorporated in the conventional capsule endoscope to receive radio-transmitted power. As shown in FIG. 16, the receiving antenna includes a receiving resonance circuit 203 having a receiving coil 201 and a receiving capacitor 202, a rectifying diode 204 that converts an alternate-current signal into a direct-current signal, and a storage capacitor 205 that stores power rectified by the rectifying diode 204. The receiving resonance circuit 203 includes the receiving coil 201 and the receiving capacitor 202 so as to have a resonance frequency that matches the frequency of a transmitted electric signal. The rectifying diode 204 rectifies the received electric signal, and the storage capacitor 205 stores the rectified electric signal. Each constituent element of the capsule endoscope operates using the power stored in the storage capacitor 205 as driving power.

Patent Document 1: Japanese Patent Application Laid-open No. 2001-231186 (Page 3, and FIG. 1)

DISCLOSURE OF INVENTION

Problem to be Solved by the Invention

However, when a transmitting antenna is mounted within a jacket that the subject wears, a problem occurs that one or both of transmission efficiency and receiving efficiency decreases. This problem is explained in further detail below.

A transmitting antenna that performs a radio transmission usually includes a resonance circuit formed with a capacitor and a coil. Therefore, usually, a resonance frequency of the resonance circuit determined based on an electrostatic capacitance of the capacitor and a self inductance of the coil is matched with a frequency of an oscillator, to perform a high-efficiency radio transmission. Accordingly, in the usual radio transmission mechanism, shapes, materials, and the like of the capacitor and the coil are determined to match the resonance frequency with the frequency of the oscillator.

On the other hand, when the transmitting antenna is built in the jacket, a value of the self inductance of the coil is not stable. Specifically, a shape and the like of the coil built in the jacket change to fit to a body shape of the subject who wears the jacket. Therefore, the value of the self inductance changes following a change in the shape and the like. Particularly, when the coil is formed to wrap around the subject, a cross-sectional area of the coil is directly influenced by the body shape of the subject, whereby the value of the self inductance of the coil changes substantially. Accordingly, there occurs a frequency difference between the resonance frequency of the resonance circuit and the frequency of the oscillator during the use, whereby transmission efficiency decreases.

The conventional radio intra-subject information acquiring system further has a problem in that there is a possibility of saturation in the value of power supplied to the capsule endoscope along the increase in power transmission strength. FIG. 17 is a schematic graph showing a voltage waveform of an electric signal output from the receiving resonance circuit 203 at the time of reception of a high-strength electric signal transmitted from the outside. In the example shown in FIG. 17, a waveform of the transmitted electric signal is a sinusoidal wave.

When the waveform of transmitted power is a sinusoidal waveform, a voltage waveform of the electric signal output from the receiving resonance circuit 203 should be a sinusoidal waveform in principle. However, when the actual capsule endoscope receives a high-strength electric signal, a waveform of a voltage is saturated at a predetermined value as shown in FIG. 17. Because a current value output from the receiving resonance circuit 203 corresponds to a value of the voltage, when saturation occurs in the voltage waveform, power obtained from the product of voltage and current is also saturated. Therefore, when power is directly acquired from the electric signal received by the receiving resonance circuit 203, the obtained power cannot be set equal to or higher than a predetermined value, regardless of the strength of the electric signal transmitted from the outside. This means that power utilization efficiency is disadvantageous, when the increase in power consumption due to the high-functional body-insertable apparatus such as a capsule endoscope is considered.

In order to avoid saturation of a voltage value, a size of the coil can be increased, for example. However, because the capsule endoscope is inserted into the subject as described above, the size of the capsule endoscope needs to be suppressed to a predetermined level or below. Thus, the increase in the coil size resulting in the increase in the size of the capsule endoscope is subjected to various constraints.

The present invention has been achieved in view of the above. It is an object of the present invention to provide a radio intra-subject information acquiring system which, while using a capsule endoscope, suppresses a decrease in one or both of transmission efficiency and receiving efficiency attributable to a variation in the self inductance of a coil which constitutes an antenna provided outside a subject.

Means for Solving Problem

A radio intra-subject information acquiring system according to one aspect of the present invention includes: a body-insertable apparatus that is inserted into a subject, the body-insertable apparatus including a receiving resonance circuit formed with a variable capacitor and a receiving coil, and a capacitance controller that changes a capacitance of the variable capacitor so as to decrease a frequency difference between a resonance frequency of the receiving resonance circuit and a frequency of a radio signal received; and a transmitting and receiving apparatus that is disposed at the outside of the subject, and performs radio communications with the body-insertable apparatus, the transmitting and receiving apparatus including a frequency variable oscillator that prescribes an oscillation frequency of a transmitted radio signal, and can adjust the oscillation frequency, a transmitting resonance circuit formed with a fixed capacitor and a transmitting coil, and a frequency controller that controls the frequency variable oscillator so as to decrease a frequency difference between the oscillation frequency and a resonance frequency of the transmitting resonance circuit that changes according to a change in a self inductance value of the transmitting coil.

In the radio intra-subject information acquiring system, the transmitting and receiving apparatus includes the frequency controller that decreases the difference between the resonance frequency of the resonance circuit and the oscillation frequency by adjusting the oscillation frequency. Therefore, reduction in the transmission efficiency caused by a change in the self inductance of the transmitting coil can be suppressed. Further, the body-insertable apparatus includes a capacitance controller that adjusts the resonance frequency of the receiving resonance circuit following the adjustment of the oscillation frequency. Therefore, a reduction in the reception efficiency can be suppressed, since the difference between the resonance frequency of the receiving resonance circuit and the oscillation frequency is decreased.

In the radio intra-subject information acquiring system, the transmitting and receiving apparatus may further include a transmitting level determining unit that determines strength of a radio signal transmitted by the transmitting resonance circuit, and the frequency controller may change the frequency while referencing the strength of the radio signal determined by the transmitting level determining unit.

In the radio intra-subject information acquiring system, the body-insertable apparatus may further include a receiving level determining unit that determines strength of a radio signal received by the receiving resonance circuit, and the capacitance controller may change a capacitance of the variable capacitor while referencing the strength of the radio signal determined by the receiving level determining unit.

In the radio intra-subject information acquiring system, the capacitance controller may change a capacitance of the variable capacitor so that strength of the radio signal becomes equal to or smaller than a permissible level.

A radio intra-subject information acquiring system according to another aspect of the present invention includes: a body-insertable apparatus that is inserted into a subject; and a transmitting and receiving apparatus that is disposed at the outside of the subject, and performs radio communications with the body-insertable apparatus, and the transmitting and receiving apparatus includes an oscillator that supplies a predetermined oscillation frequency, a transmitting resonance circuit that is formed with a variable capacitor and a transmitting coil, and a capacitance controller that changes a capacitance of the variable capacitor so as to decrease a frequency difference between the oscillation frequency and a resonance frequency of the transmitting resonance circuit generated according to a change in a self inductance of the transmitting coil.

In the radio intra-subject information acquiring system, the transmitting and receiving apparatus that adjusts the capacitance of the transmitting resonance circuit includes the capacitance controller. Therefore, a reduction in the transmission efficiency can be suppressed by decreasing a variation width of the resonance frequency caused by a change in self inductance of the transmitting coil, and by decreasing a frequency difference between the resonance frequency and the oscillation frequency.

In the radio intra-subject information acquiring system, the transmitting and receiving apparatus may further include a transmitting level determining unit that determines strength of a radio signal to be transmitted by the transmitting resonance circuit, and the capacitance controller may change a capacitance while referencing strength of a radio signal determined by the transmitting level determining unit.

In the radio intra-subject information acquiring system, the radio intra-subject information acquiring system may further include a wearing member that the subject wears at the time the body-insertable apparatus is inserted into the subject, and the transmitting coil may be disposed on the wearing member.

In the radio intra-subject information acquiring system, the transmitting coil may be formed to wrap around the subject when the subject wears the wearing member.

In the radio intra-subject information acquiring system, the variable capacitor may be formed with a variable capacitance diode.

In the radio intra-subject information acquiring system, the variable capacitor may be formed with plural mechanisms connected in parallel, each mechanism including a fixed capacitor and a switching unit connected with each other, and a capacitance may change when the switching unit is turned on and off.

In the radio intra-subject information acquiring system, the transmitting and receiving apparatus may transmit a radio signal including at least a power supply signal, which is to be converted into driving power inside the body-insertable apparatus, to the body-insertable apparatus.

A radio intra-subject information acquiring system according to still another aspect of the present invention includes: a body-insertable apparatus that is inserted into a subject, the body-insertable apparatus including, a receiving resonance circuit having a receiving coil and a receiving capacitor, and a voltage converter that converts a voltage of an electric signal received by the receiving resonance circuit into a value lower than induced electromotive force generated in the receiving coil; and a power supply apparatus that is disposed at the outside of the subject, and supplies power to the body-insertable apparatus by radio transmission.

In the radio intra-subject information acquiring system, the body-insertable apparatus does not directly extract power from an electric signal acquired by the receiving resonance circuit. The body-insertable apparatus extracts power, after converting a voltage of an electric signal received by the receiving resonance circuit into a value lower than induced electromotive force in the receiving coil. Therefore, saturation of a voltage value of the electric signal extracted as power can be prevented.

In the radio intra-subject information acquiring system, the voltage converter may include a power supply coil that generates induced electromotive force based on a magnetic field generated during a reception by the receiving coil.

In the radio intra-subject information acquiring system, the power supply coil may have a smaller number of winding than a winding of the receiving coil.

In the radio intra-subject information acquiring system, the power supply coil may be formed in a state where an internal periphery of the power supply coil is in contact with an external periphery of the receiving coil.

In the radio intra-subject information acquiring system, the internal periphery of the power supply coil is closely contacted to the external periphery of the receiving coil. Therefore, despite a disposal of an additional power supply coil, an area occupied by the coil does not increase, and the increase in the size of the body-insertable apparatus can be suppressed.

In the radio intra-subject information acquiring system, the body-insertable apparatus may include a separator that separates a power supply signal from an electric signal of which voltage is converted by the voltage converter, a power reproducing unit that reproduces power based on the separated power supply signal; and a capacitor that stores reproduced power.

Effect of the Invention

According to the radio intra-subject information acquiring system of the present invention, the transmitting and receiving apparatus includes a frequency controller that decreases a difference between the resonance frequency of the resonance circuit and the oscillation frequency by adjusting the oscillation frequency. Therefore, there is an effect that reduction in the transmission efficiency generated due to a change in the self inductance of the transmitting coil can be suppressed. Further, the body-insertable apparatus includes a capacitance controller that adjusts the resonance frequency of the receiving resonance circuit following the adjustment of the oscillation frequency. Therefore, there is an effect that a reduction in the reception efficiency can be suppressed, by decreasing a difference between the resonance frequency of the receiving resonance circuit and the oscillation frequency.

According to the radio intra-subject information acquiring system of the present invention, a transmitting and receiving apparatus that adjusts the capacitance of the transmitting resonance circuit includes a capacitance controller. Therefore, there is an effect that a reduction in the transmission efficiency can be suppressed by decreasing a variation width of a resonance frequency generated due to a change in a self inductance of the transmitting coil, and by decreasing a frequency difference between the resonance frequency and an oscillation frequency.

According to the radio intra-subject information acquiring system of the present invention, the body-insertable apparatus does not directly extract power from an electric signal acquired by the receiving resonance circuit. The body-insertable apparatus extracts power, after converting a voltage of an electric signal received by the receiving resonance circuit into a value lower than induced electromotive force in the receiving coil. Therefore, there is an effect that a radio intra-subject information acquiring system can be achieved that can prevent saturation of a voltage value of the electric signal extracted as power, and can prevent saturation of power supplied from the transmitting and receiving apparatus.

According to the radio intra-subject information acquiring system of the present invention, the internal periphery of the power supply coil is closely contacted to the external periphery of the receiving coil. Therefore, there is an effect that, despite a disposal of an additional power supply coil, an area occupied by the coil does not increase, and saturation of power can be suppressed while suppressing the increase in the size of the body-insertable apparatus.

EXPLANATIONS OF LETTERS OR NUMERALS

Figure 1:
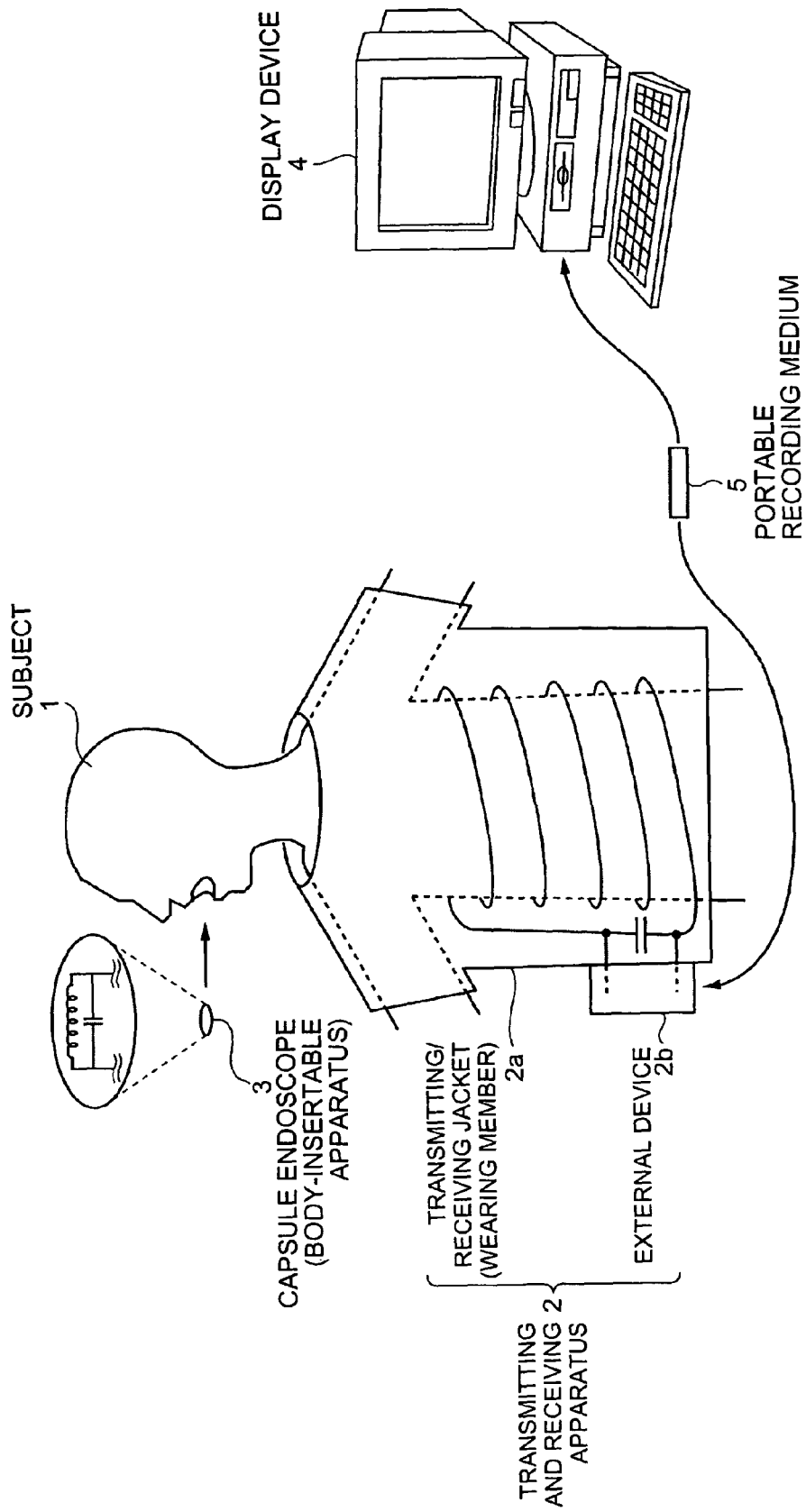
FIG. 1 is a schematic diagram showing an overall configuration of a radio intra-subject information acquiring system according to the present invention.

1 Subject
2 Transmitting and receiving apparatus
2a Transmitting/receiving jacket
2b External device
3 Capsule endoscope
4 Display device
5 Portable recording medium
11 Receiving antenna unit 12 RF receiving unit
13 Image processing unit
14 Storage unit
15 Control information input unit
16 Frequency variable oscillator
17 Superimposing circuit
18 Amplifier circuit
20 Transmitting antenna unit
22 Transmitting resonance circuit
23 Fixed capacitor
24 Transmitting coil
25 Transmitting level determining unit
26 Frequency controller
31 LED
32 LED driving circuit
33 CCD
34 CCD driving circuit
35 RF transmitting unit
36 Transmitting antenna unit
37 Receiving antenna unit
38 Separating circuit
39 Power reproducing circuit
40 Receiving level determining unit
41 Booster circuit
42 Capacitor
43 System control circuit
44 Control information detecting circuit
45 Receiving resonance circuit
46 Receiving coil
47 Variable capacitor
48 Capacitance controller
51 Transmitting and receiving apparatus
51a Transmitting/receiving jacket
51b External device
52 Capsule endoscope
53 Oscillator
54 Transmitting antenna unit
55 Transmitting resonance circuit
56 Variable capacitor
57 Capacitance controller
62 Receiving antenna unit
63 Receiving resonance circuit
64 Fixed capacitor
65 Transmitting and receiving apparatus
65a Transmitting/receiving jacket
65b External device
66 Acceleration determining unit
101 Subject
102 Transmitting and receiving apparatus
102a Transmitting/receiving jacket
102b External device
103 Capsule endoscope
104 Display device
105 Portable recording medium
111 RF receiving unit
112 Image processing unit
113 Storage unit
114 Oscillator
115 Control information input unit
116 Superimposing circuit
117 Amplifier circuit
118 Power supply unit
119 LED
120 LED driving circuit
121 CCD
122 CCD driving circuit
123 RF transmitting unit
124 Transmitting antenna unit
125 Receiving antenna unit
126 Voltage converting circuit
127 Separating circuit
128 Power reproducing circuit
129 Booster circuit
130 Capacitor
131 Control information detecting circuit
132 System control circuit
133 Receiving resonance circuit
134 Receiving coil
135 Receiving capacitor
136 Power supply coil

BEST MODE(S) FOR CARRYING OUT THE INVENTION

A radio intra-subject information acquiring system according to best modes for carrying out the invention will be explained below. Note that the drawings are schematic, and that a relationship between a thickness and a width of each part, and a rate of a thickness of each part are different from actual data. Needless to mention, a size relationship and rates are different between the drawings. In the following embodiments, explanations are given based on a capsule endoscope system that images a body cavity, as an example. However, it is needless to mention that intra-subject information is not limited to body-cavity images.

First Embodiment

First, a radio intra-subject information acquiring system according to a first embodiment is explained. FIG. 1 is a schematic diagram showing an overall configuration of the radio intra-subject information acquiring system during a usage. As shown in FIG. 1, the radio intra-subject information acquiring system includes: a capsule endoscope 3 that functions as one example of a body-insertable apparatus, and has a resonance circuit to receive a radio signal; a transmitting and receiving apparatus 2 that has a function of performing radio transmission and reception to and from the capsule endoscope 3; a display device 4 that displays a body-cavity image based on data received by the transmitting and receiving apparatus 2; and a portable recording medium 5 that delivers data between the transmitting and receiving apparatus 2 and the display device 4.

The display device 4 displays a body-cavity image picked up by the capsule endoscope 3, and has a configuration that displays images based on data acquired from the portable recording medium 5. Specifically, the display device 4 can have a configuration that directly displays images by a CRT display, a liquid crystal display, or the like, or have a configuration that outputs images to other medium as in a printer.

The portable recording medium 5 is attachable to and detachable from an external device 2b and the display device 4, and can output or record information when the portable recording medium 5 is mounted on either of the two. Specifically, during a period while the capsule endoscope 3 is moving within the body cavity of the subject 1, the portable recording medium 5 is mounted on the external device 2b and records data transmitted from the capsule endoscope 3. After the capsule endoscope is discharged from the subject 1, the portable recording medium 5 is removed from the external device 2b and is mounted on the display device 4 so that the display device 4 reads out the recorded data. Because the portable recording medium 5 delivers data between the external device 2b and the display device 4, the subject 1 can move freely during a period while the capsule endoscope images the body cavity, unlike when the external device 2b is connected to the display device 4 by wire.

The transmitting and receiving apparatus 2 includes a transmitting/receiving jacket 2a, in a shape that the subject 1 can wear, to function as an example of a wearing member, and an external device 2b that has a function of processing data received by the transmitting/receiving jacket 2a. The transmitting/receiving jacket 2a includes a transmitting coil 24 that is formed to wrap around the subject 1 when the subject 1 wears the transmitting/receiving jacket 2a, and a fixed capacitor 23 that is formed with a capacitor or the like and has a fixed capacitance. The transmitting coil 24 and the fixed capacitor 23 forms a resonance circuit.

Figure 2:
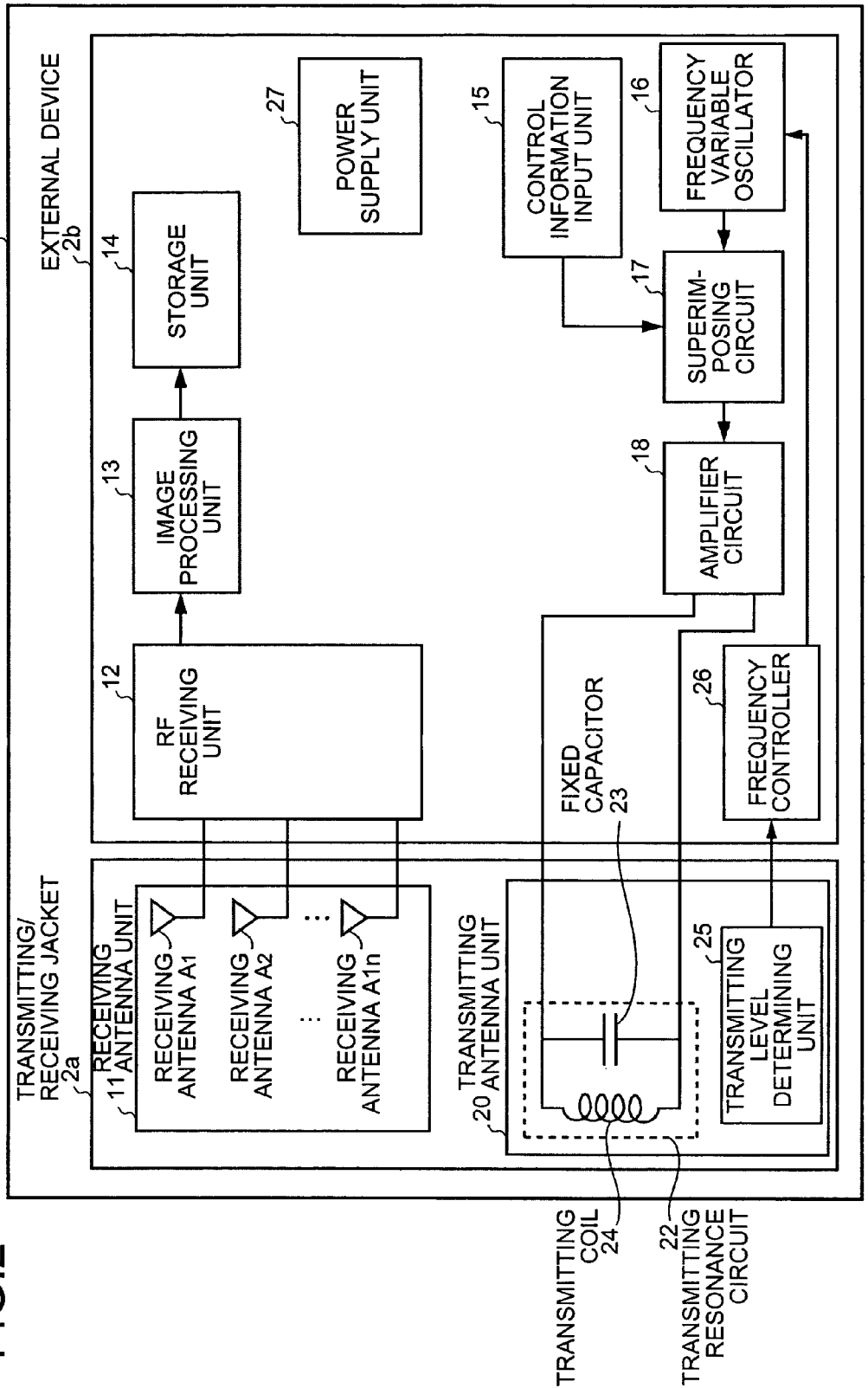
FIG. 2 is a block diagram showing a configuration of a transmitting and receiving apparatus according to a first embodiment.

FIG. 2 is a block diagram schematically showing a detailed configuration of the transmitting and receiving apparatus 2. As shown in FIG. 2, the transmitting and receiving apparatus 2 includes a receiving antenna unit 11, and a transmitting antenna unit 20 on the transmitting/receiving jacket 2a, and includes a mechanism that performs signal processing on the external device 2b.

The external device 2b has a mechanism that processes received data. Specifically, the external device 2b includes an RF receiving unit 12 that performs a predetermined process to a radio signal received by the receiving antenna unit 11, and outputs image data of the body cavity imaged by the capsule endoscope, an image processing unit 13 that executes predetermined image processing to the output image data, and a storage unit 14 that stores image-processed image data. Image-processed image data is recorded into the portable recording medium 5 via the storage unit 14.

The external device 2b also includes a mechanism that generates a signal to be transmitted to the capsule endoscope 3. Specifically, the external device 2b includes: a control information input unit 15 that inputs a control information signal to execute a drive control of the mechanism within the capsule endoscope 3; a frequency variable oscillator 16 having a mechanism that prescribes an oscillation frequency of a radio signal including a power supply signal which is a target of transmission, and that can change a frequency; a superimposing circuit 17 that combines a control information signal and an oscillation frequency; and an amplifier circuit 18 that amplifies a signal combined by the superimposing circuit 17.

The transmitting antenna unit 20 includes a transmitting resonance circuit 22 formed with a fixed capacitor 23 and a transmitting coil 24, and a transmitting level determining unit 25 that detects strength of a radio signal transmitted from the transmitting resonance circuit 22. Strength detected by the transmitting level determining unit 25 is output to a frequency controller 26 provided within the external device 2b. The frequency controller 26 changes the value of the frequency oscillated by the frequency variable oscillator 16 based on detected strength.

The capsule endoscope 3 is explained next. The capsule endoscope 3 is inserted into the body cavity of the subject 1, and has a function of imaging the body cavity, and radio transmitting the acquired image, and receives a power supply signal and the like from the transmitting/receiving jacket 2a to secure driving force, for example.

Figure 3:
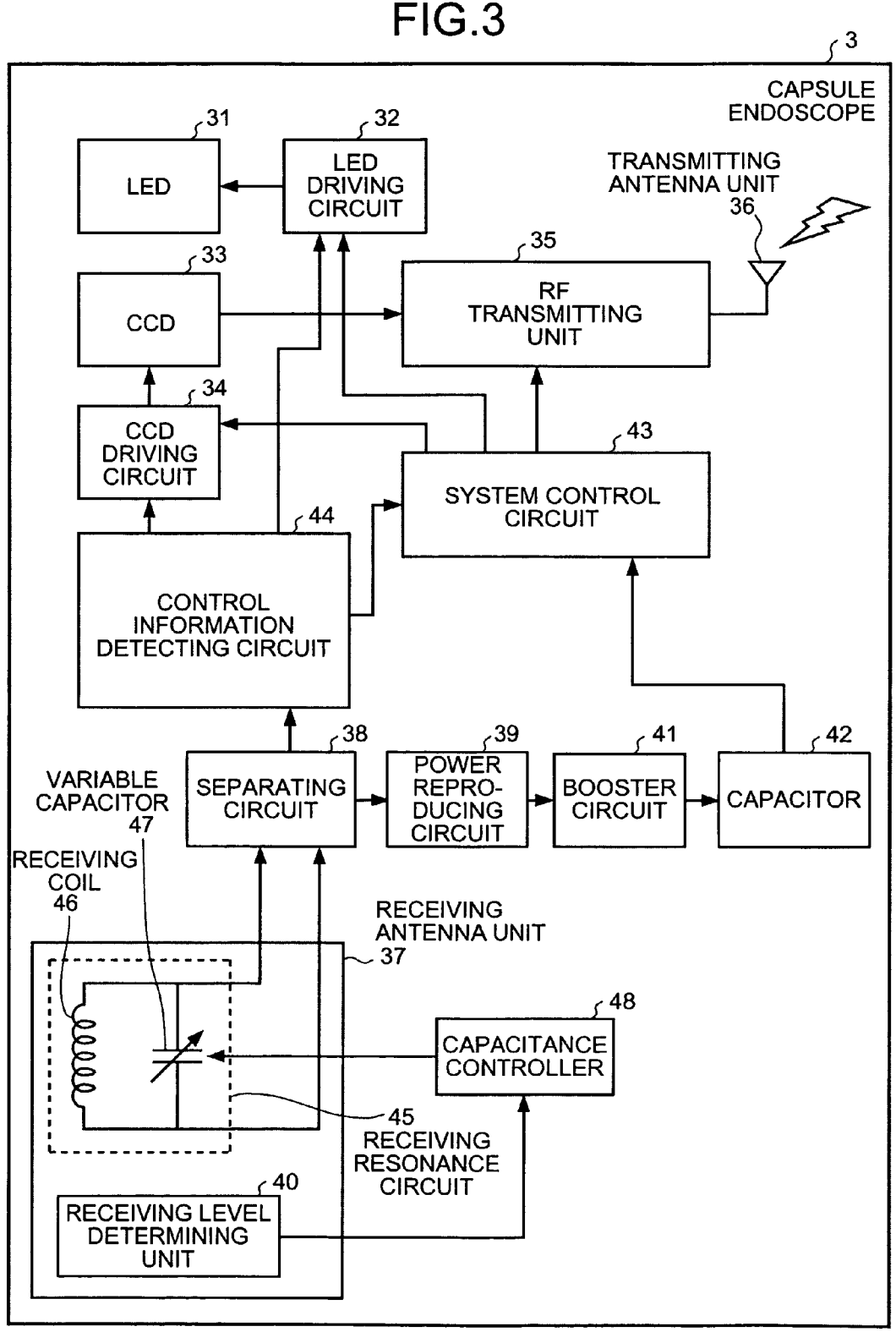
FIG. 3 is a block diagram showing a configuration of a capsule endoscope according to the first embodiment.

FIG. 3 is a block diagram schematically showing the configuration of the capsule endoscope 3. As shown in FIG. 3, the capsule endoscope 3 includes: an LED 31 as a light-emitting element that emits illumination light to illuminate an examined area of the subject 1; an LED driving circuit 32 that transmits an LED driving signal to drive the LED 31; a CCD 33 that images the subject by receiving the illumination light emitted from the LED 31 and reflected by the examined area of the subject; a CCD driving circuit 34 that drives the CCD 33; an RF transmitting unit 35 that modulates an image signal output from the CCD 33 to obtain an RF signal; and a transmitting antenna unit 36 as a transmitting antenna that performs radio transmission of an RF signal output from the RF transmitting unit 35.

The capsule endoscope 3 further includes: a receiving antenna unit 37 that receives a radio signal sent from the transmitting and receiving apparatus 2; a separating circuit 38 that separates a power supply signal from a signal received by the receiving antenna unit 37; a power reproducing circuit 39 that reproduces power from the power supply signal; a booster circuit 41 that boosts reproduced power; a capacitor 42 that stores boosted power; and a system control circuit 43 that controls each unit within the capsule endoscope 3 such as the CCD 33 and the LED 31, based on power stored in the capacitor 42 and a control information signal extracted by a control information detecting circuit 44. The capsule endoscope 3 further includes a capacitance controller 48 that controls a capacitance of a variable capacitor 47 provided in the receiving antenna unit 37 described later, based on a power level acquired by a receiving level determining unit 40 described later.

The receiving antenna unit 37 includes a receiving coil 46, a receiving resonance circuit 45 formed with the variable capacitor 47, and the receiving level determining unit 40 that detects strength of a radio signal received by the receiving resonance circuit 45 near the receiving resonance circuit 45. The receiving resonance circuit 45 has a resonance frequency determined by a self inductance of the receiving coil 46 and a capacitance of the variable capacitor 47. The variable capacitor 47 is formed by parallel connecting plural mechanisms each having a variable capacitance diode, a fixed capacitor, and switching unit, for example. The variable capacitor 47 has a mechanism whose capacitance changes when the switching unit is turned on and off, and has a function that the capacitance changes based on the control of the capacitance controller 48.

The receiving antenna unit 37 can change a resonance frequency of the receiving resonance circuit 45, by changing the capacitance of the variable capacitor 47. Specifically, the value of the capacitance of the variable capacitor 47 changes according to the control of the capacitance controller 48. The capacitance controller 48 has a function of adjusting the capacitance of the variable capacitor 47 based on the strength of a radio signal acquired by the receiving level determining unit 40.

The operation of the radio intra-subject information acquiring system according to the first embodiment is explained next. As described above, it is known that when the transmitting coil 24 for transmission is built into the transmitting/receiving jacket, a shape and the like of the transmitting coil 24 for transmission change according to a body type of the subject 1 who wears the transmitting/receiving jacket. Due to a change of the shape and the like, a value of the self inductance of the transmitting coil 24 changes, and a resonance frequency of the transmitting resonance circuit 22 changes. Therefore, even if the oscillation frequency of a radio signal and the resonance frequency of the transmitting resonance circuit 22 coincide with each other in the initial state, when the subject 1 wears the transmitting/receiving jacket 2a, a difference occurs between the oscillation frequency and the resonance frequency, and the transmission efficiency of a transmission from the transmitting and receiving apparatus 2 and the reception efficiency in the capsule endoscope 3 decrease. Accordingly, in the first embodiment, the oscillation frequency of the transmitting and receiving apparatus 2 is adjusted, and the capacitance of the variable capacitor 47 in the capsule endoscope 3 is adjusted, against the variation in the resonance frequency.

Figure 4:
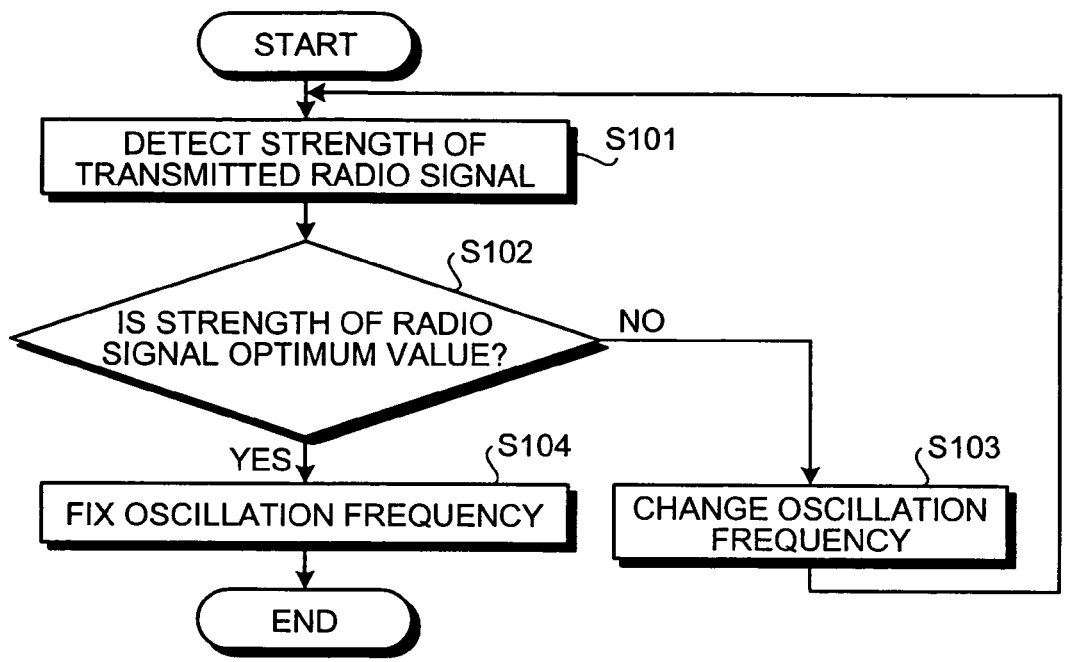
FIG. 4 is a flowchart for explaining an adjustment operation of an oscillation frequency of the transmitting and receiving apparatus.

FIG. 4 is a flowchart for explaining the adjustment operation of an oscillation frequency in the transmitting and receiving apparatus 2. First, the transmitting level determining unit 25 determines strength of a radio signal transmitted from the transmitting antenna unit 20 (step S101). The transmitting level determining unit 25 outputs information concerning the strength of a radio signal determined at step S101, to the frequency controller 26, and the frequency controller 26 determines whether the strength of the radio signal is an optimum value (step S102).

When it is determined that the strength of the radio signal is an optimum value, it is determined that the oscillation frequency substantially coincides with the resonance frequency of the transmitting resonance circuit 22. Therefore, the value of the oscillation frequency is maintained as it is (step S104), and the adjustment of the oscillation frequency ends. When it is determined that the strength of the radio signal is not an optimum value, the value of the oscillation frequency is changed (step S103), and the process returns to step S101 again. The above operation is repeated.

As described above, the transmitting coil 24 is provided on the transmitting/receiving jacket 2a. Because the shape of the transmitting coil 24 is influenced by the body type and the like of the subject 1, the value of the self inductance changes. On the other hand, the resonance frequency of the transmitting resonance circuit 22 is determined by the self inductance of the transmitting coil 24 and the capacitance of the fixed capacitor 23. Therefore, due to the variation of the value of the self inductance, the resonance frequency of the transmitting resonance circuit 22 changes. A difference occurs between the resonance frequency and the oscillation frequency prescribed by the frequency variable oscillator 16. As a result, transmission efficiency decreases. Therefore, the transmitting and receiving apparatus 2 adjusts the oscillation frequency, against the change of the resonance frequency due to the change in the self inductance of the transmitting coil 24, thereby decreasing a difference between the resonance frequency and the oscillation frequency, and suppressing a decrease in the transmission efficiency.

An optimum value of a radio signal transmitted at step S102 can be optional, depending on characteristics of a transmission mechanism, for example. When the transmitting level determining unit 25 has a configuration that detects a value of a current flowing through the transmitting oscillation circuit 22, for example, a current that theoretically flows through the transmitting resonance circuit 22 can be used as an optimum value. At step S102, it can be determined that a radio signal reaches the optimum value when a difference between the current value and a predetermined value is suppressed to within a predetermined range, as well as when the current value accurately coincides with the optimum value.

At step S104, while a change of the oscillation frequency can be determined at random, the oscillation frequency can be adjusted to an optimum oscillation frequency more quickly, with the use of what is called a Hill-climbing method. Alternatively, a changed frequency can be determined based on an optional algorithm.

Figure 5:
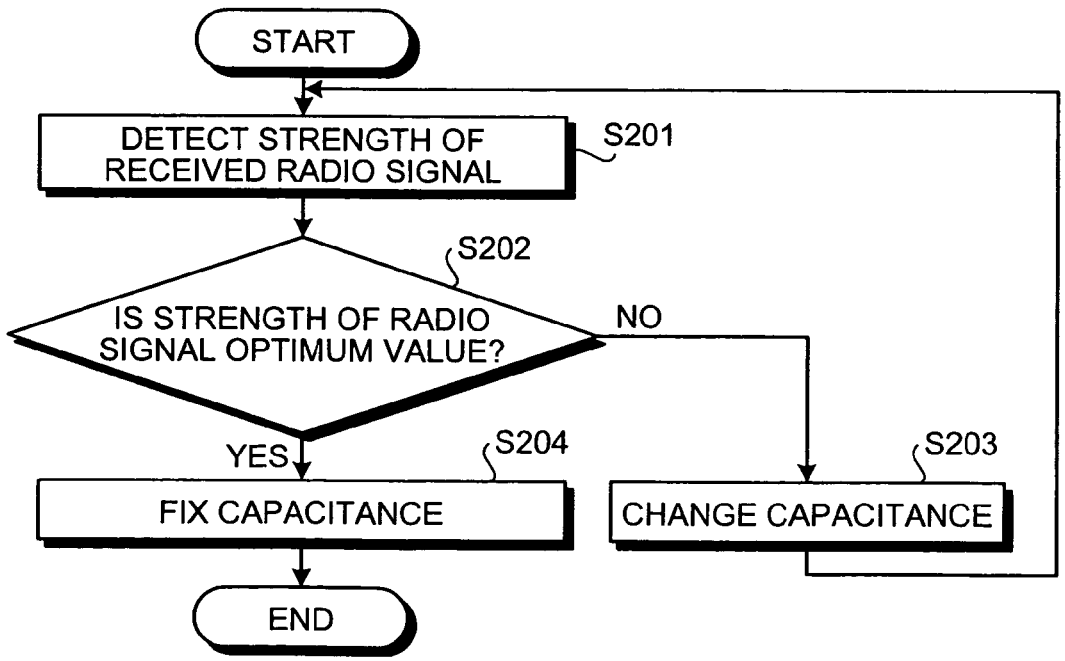
FIG. 5 is a flowchart for explaining an adjustment operation of a capacitance of a capsule endoscope.

The adjustment operation of the variable capacitor 47 in the capsule endoscope 3 is explained next. FIG. 5 is a flowchart for explaining the adjustment operation of the variable capacitor 47 in the capsule endoscope 3. First, the receiving level determining unit 40 detects strength of a received radio signal (step S201). Detected strength is output to the capacitance controller 48. The capacitance controller 48 determines whether the strength of a radio signal has reached an optimum value (step S202).

When it is determined that the strength of a radio signal is different from the optimum value, the capacitance controller 48 changes the value of the capacitance of the variable capacitor 47, to change the resonance frequency of the receiving resonance circuit 45. The process returns to step S201 again, and a similar operation is repeated. Therefore, the adjustment of the value of the capacitance of the variable capacitor 47 is repeated until the strength of the received radio signal reaches the optimum value. On the other hand, when it is determined at step S202 that the strength of a radio signal has reached an optimum value, the capacitance of the variable capacitor 47 is fixed, and the adjustment operation ends.

As described above, according to the first embodiment, the transmitting and receiving apparatus 2 has a configuration that changes the oscillation frequency according to a variation in the self inductance of the transmitting coil 24. Due to the change in the oscillation frequency, a difference occurs between the frequency of the radio signal received by the capsule endoscope 3, which is a receiver side, and the resonance frequency of the receiving resonance circuit 45, and the reception efficiency decreases. Therefore, in the first embodiment, not only the frequency in the transmitting and receiving apparatus 2 having a changing shape of the transmitting coil 24 is adjusted, but also the resonance frequency of the receiving resonance circuit 45 provided in the capsule endoscope 3 is adjusted, whereby a decrease in the efficiency of radio communication is suppressed.

Though the optimum value that is a determination standard is optionally determined according to the characteristics of the receiving mechanism at step S202, it is preferable that the optimum value be set for a current that flows through the resonance circuit and for a voltage between predetermined two points in the resonance circuit, like at step S102. At step S203, the capacitance can be changed to a capacitance extracted at random, like at step S103, or the capacitance to be changed can be determined based on the Hill-climbing method.

As explained above, the radio intra-subject information acquiring system according to the first embodiment has an advantage in that a reduction in the transmission efficiency and reception efficiency can be suppressed, by changing the oscillation frequency of the transmitting and receiving apparatus 2 at the transmission side, and by changing the resonance frequency of the receiving resonance circuit 45 in the capsule endoscope 3 at the receiving side, against a variation of the self inductance value due to a change in the shape of the transmitting coil 24.

A change in the self inductance value due to a change of shape and the like of the transmitting coil 24 is different depending on a body type of the subject 1. Therefore, in the first embodiment, the oscillation frequency and the like are adjusted each time the subject 1 wears the transmitting/receiving jacket 2a. With this arrangement, a reduction in the transmission efficiency can be suppressed, regardless of a difference of body type and the like of the subject 1.

Along the adjustment of the oscillation frequency at the transmitting and receiving apparatus 2 side, the capacitance of the variable capacitor 47 provided in the capsule endoscope 3 is adjusted in the first embodiment. With this arrangement, a frequency difference between the resonance frequency of the receiving resonance circuit 45 provided in the capsule endoscope 3 and the frequency of the radio signal, that is, the oscillation frequency adjusted as described above, is decreased, and a reduction in the reception efficiency at the capsule endoscope 3 side can be suppressed.

Second Embodiment

A radio intra-subject information acquiring system according to a second embodiment is explained next. In the second embodiment, a reduction of transmission efficiency is suppressed by changing a capacitance of the variable capacitor provided within a transmitting/receiving jacket, according to a variation in the value of a self inductance of a coil provided in the transmitting/receiving jacket.

Figure 6:
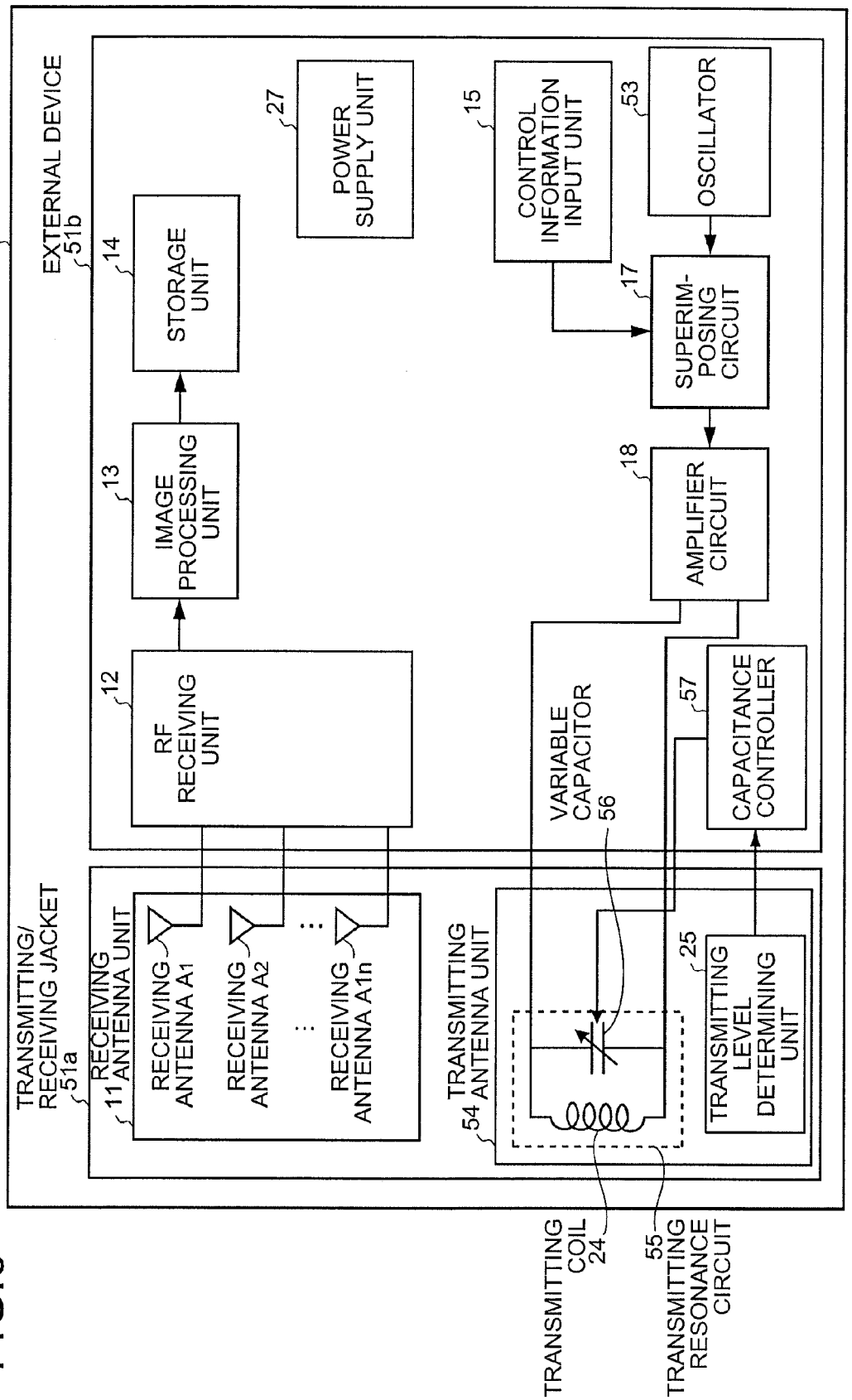
FIG. 6 is a block diagram showing a configuration of a transmitting and receiving apparatus according to a second embodiment.
Figure 7:
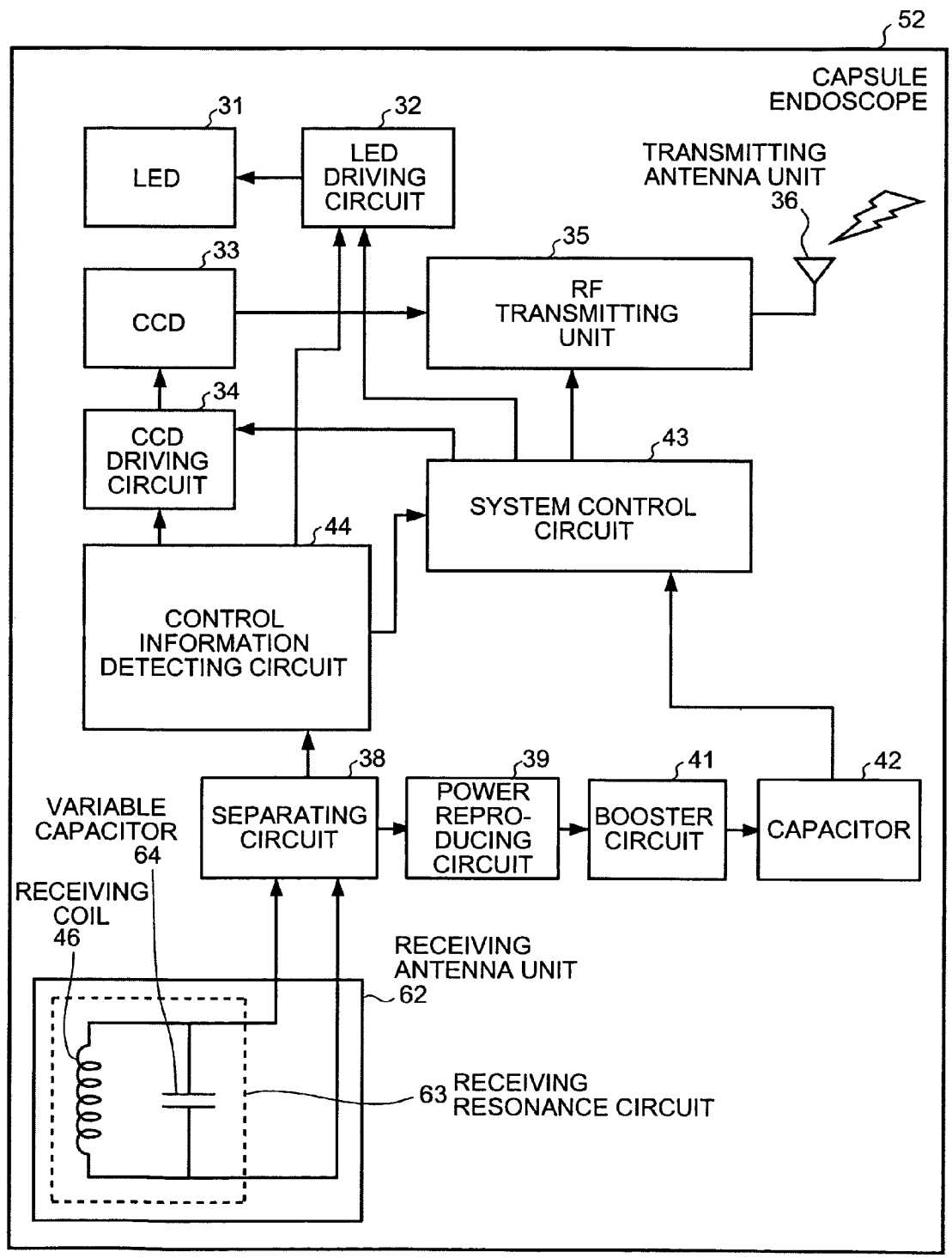
FIG. 7 is a block diagram showing a configuration of a capsule endoscope according to the second embodiment.

FIG. 6 is a block diagram schematically showing a configuration of a transmitting and receiving apparatus 51 according to the second embodiment, and FIG. 7 is a block diagram schematically showing a configuration of a capsule endoscope 52 according to the second embodiment. In the second embodiment, an overall configuration of the radio intra-subject information acquiring system is similar to that of the first embodiment unless otherwise specified below. In FIG. 6 and FIG. 7, configurations and functions of constituent elements having names or reference symbols common to those in the first embodiment are similar to those of the first embodiment unless otherwise specified below.

First, the configuration of the transmitting and receiving apparatus 51 is explained with reference to FIG. 6. In the second embodiment, an oscillator 53 provided in an external device 51b has a configuration that transmits a signal in a predetermined frequency, unlike the frequency variable oscillator 16 in the first embodiment. A transmitting antenna unit 54 provided within a transmitting/receiving jacket 51a includes a transmitting resonance circuit 55 formed with the transmitting coil 24 and a variable capacitor 56, the transmitting level determining unit 25 that detects strength of a radio signal transmitted by the transmitting resonance circuit 55, and a capacitance controller 57 that controls the capacitance of the variable capacitor 56 based on strength of a radio signal.

The configuration of the capsule endoscope 52 that functions as one example of a body-insertable apparatus is explained with reference to FIG. 7. In the second embodiment, a resonance frequency of the receiving resonance circuit 63 disposed within the receiving antenna unit 62 provided in the capsule endoscope 52 is not adjusted. A fixed capacitor 64 that forms the receiving resonance circuit 63 has a fixed capacitance, and a receiving level determining unit and a capacitance controller are not provided.

Figure 8:
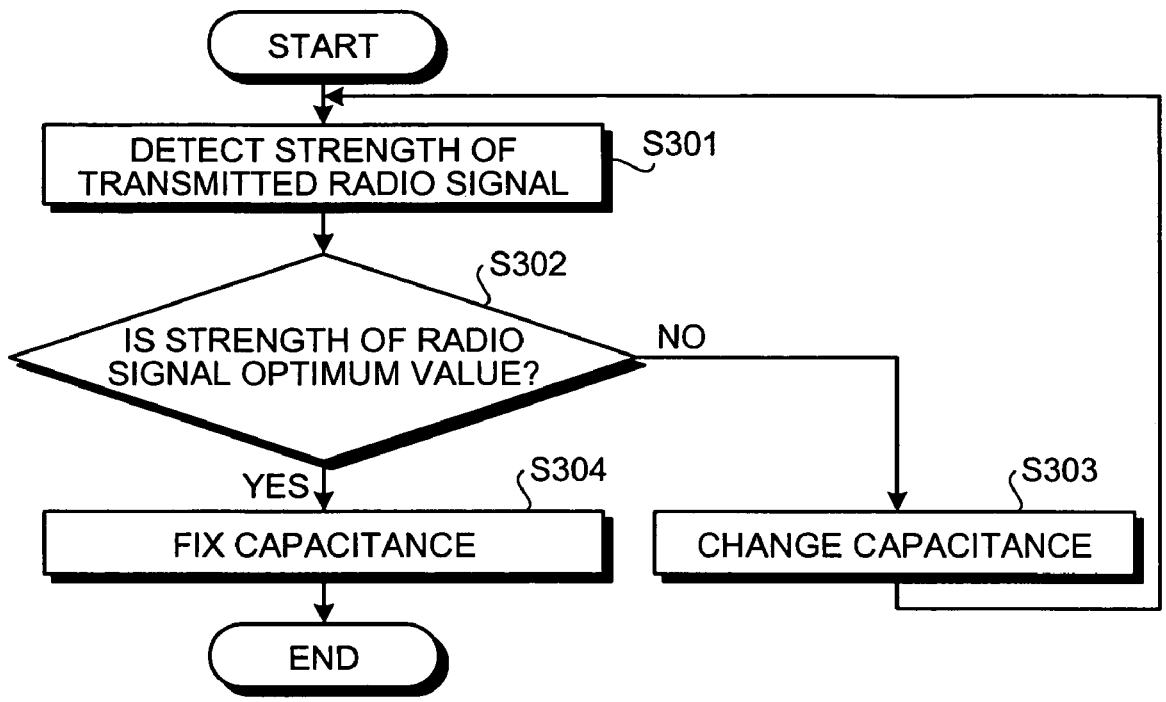
FIG. 8 is a flowchart for explaining an adjustment operation of a capacitance of the transmitting and receiving apparatus.

In the second embodiment, against a variation in the self inductance value of the transmitting coil 24 provided in the transmitting and receiving apparatus 51, the capacitance of the variable capacitor 56 that forms the transmitting resonance circuit 55 with the transmitting coil 24 is adjusted. Adjustment operation of the variable capacitor 56 in the transmitting and receiving apparatus 51 is explained below with reference to a flowchart shown in FIG. 8.

First, the transmitting level determining unit 25 detects strength of a transmitted radio signal (step S301). Detected strength is output to the capacitance controller 57. The capacitance controller 57 determines whether the strength of the radio signal reaches an optimum value (step S302).

When it is determined that the strength of the radio signal does not reach the optimum value, the capacitance controller 57 changes the capacitance of the variable capacitor 56 (step S303), and repeats the above operation by returning to step S301. Therefore, the capacitance of the variable capacitor 56 is adjusted until the strength of the transmitted radio signal reaches the optimum value. On the other hand, when it is determined at step S302 that the strength of the radio signal reaches the optimum value, the capacitance controller 57 fixes the capacitance of the variable capacitor 56 (step S304), thereby ending the adjustment.

In the second embodiment, a reduction of transmission efficiency is suppressed, by adjusting the capacitance of the variable capacitor 56 provided within the transmitting and receiving apparatus 51. When the self inductance of the transmitting coil 24 changes, the resonance frequency of the transmitting resonance circuit 55 including the transmitting coil 24 comes to take a value different from the oscillation frequency supplied by the oscillator 53. On the other hand, in the second embodiment, the resonance frequency of the transmitting resonance circuit 55 is adjusted by changing the capacitance of the variable capacitor 56 that forms the transmitting resonance circuit 55 with the transmitting coil 24, whereby a difference between the oscillation frequency supplied from the oscillator 53 and the resonance frequency is decreased. As a result, a reduction in transmission efficiency is suppressed.

The control of the resonance frequency of the transmitting resonance circuit 55 provided within the transmitting and receiving apparatus 51 so as to decrease a difference between the resonance frequency and the oscillation frequency supplied from the oscillator 53 is advantageous in that the adjustment of the resonance frequency in the capsule endoscope 52 becomes unnecessary. Specifically, in the second embodiment, the oscillation frequency supplied from the oscillator 53 is maintained at the initial value in the transmitting and receiving apparatus 51. Therefore, the frequency of a radio signal transmitted from the transmitting and receiving apparatus 51 does not change from the initial value. On the other hand, the receiving resonance circuit 63 provided in the capsule endoscope 52 is formed in advance such that the resonance frequency coincides with the oscillation frequency supplied from the oscillator 53. Therefore, when the oscillation frequency is not adjusted as in the second embodiment, the frequency of a radio signal received by the capsule endoscope 52 does not change, and efficient reception is possible without providing a mechanism that adjusts the resonance frequency of the receiving resonance circuit 63. Therefore, the radio intra-subject information acquiring system according to the second embodiment has an advantage in that the capsule endoscope 52 can be achieved in a simple configuration.

Modified Example

A modified example of the second embodiment is explained next. In this modified example, a capacitance of a variable capacitor is adjusted each time a subject who wears a transmitting/receiving jacket changes a posture.

In the first and the second embodiments, the fact that a self inductance value of a coil provided within the transmitting/receiving jacket changes for each subject is taken up as a problem, and a reduction in one or both of transmission efficiency and reception efficiency is suppressed by adjusting a capacitance of a variable capacitor. However, a shape and the like of the coil provided in the transmitting/receiving jacket change again when the subject changes a posture after wearing the transmitting/receiving jacket, not only when the subject wears the transmitting/receiving jacket.

Therefore, in the modified example, the external device includes a mechanism that detects the motion of the subject, and this mechanism adjusts a capacitance of a variable capacitor each time the subject moves. A configuration of a transmitting and receiving apparatus according to the modified example having the above configuration, and an adjustment operation of a capacitance of the variable capacitor are explained below.

Figure 9:
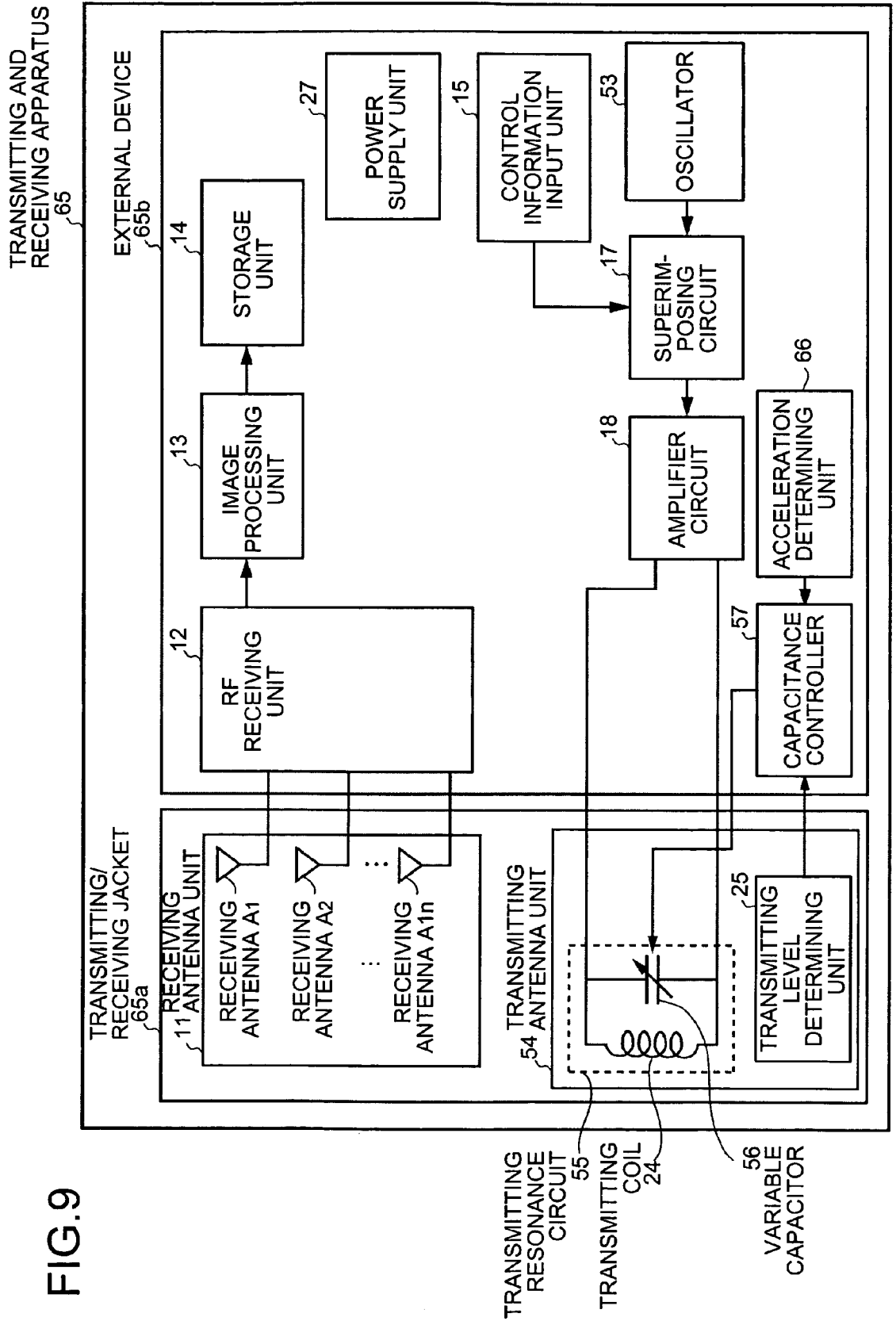
FIG. 9 is a block diagram showing a configuration of a transmitting and receiving apparatus according to a modified example of the second embodiment.

FIG. 9 is a block diagram showing a configuration of a transmitting and receiving apparatus 65 constituting a radio intra-subject information acquiring system according to the modified example. Note that configurations of constituent elements other than the transmitting and receiving apparatus 65 are similar to those of the second embodiment.

The transmitting and receiving apparatus 65 includes, in an external device 65b, an acceleration determining unit 66 that detects a move or a change of a posture of the subject 1 while the subject 1 wears a transmitting/receiving jacket 65a. The transmitting level determining unit 25 starts a detection operation, based on a result of detection executed by the acceleration determining unit 66.

Figure 10:
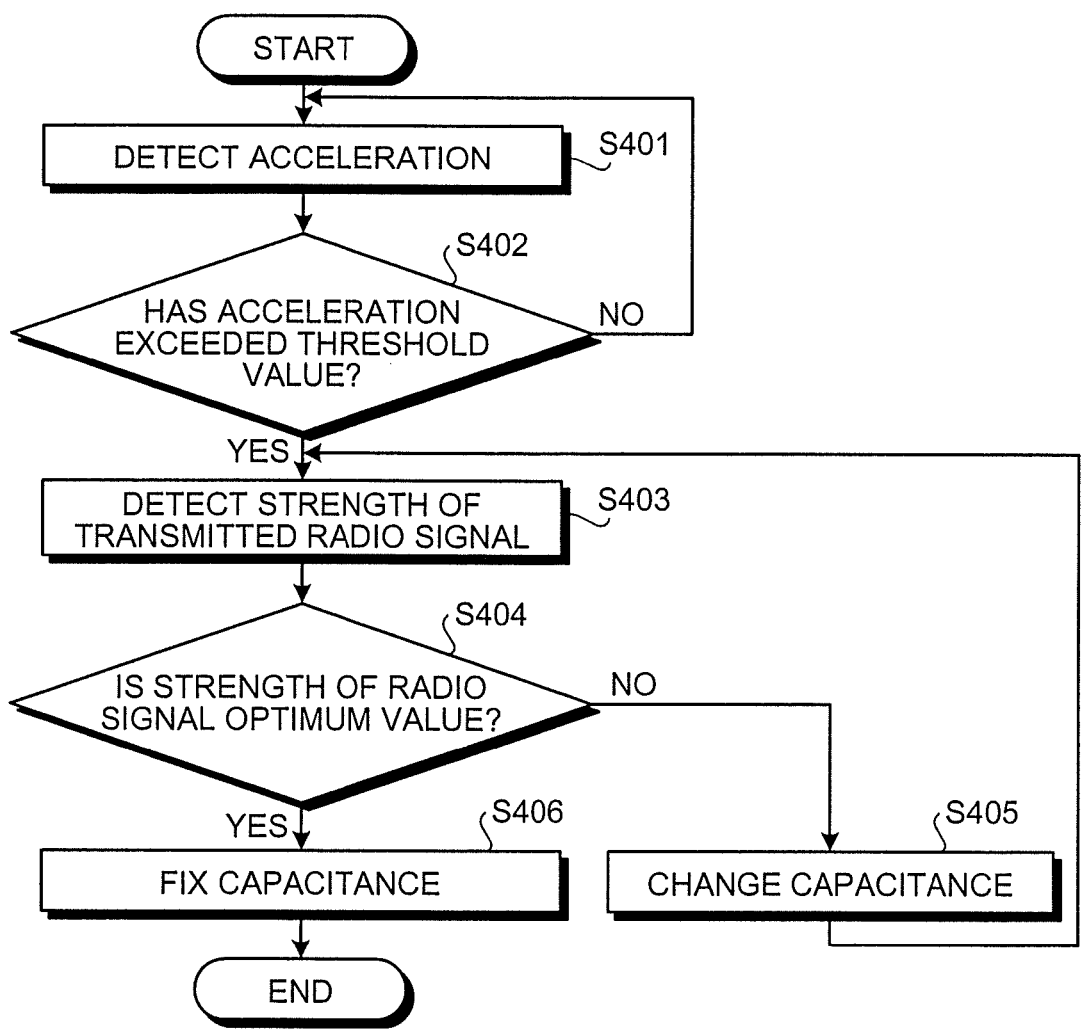
FIG. 10 is a flowchart for explaining an adjustment operation of a capacitance of the transmitting and receiving apparatus.

The adjustment operation of a capacitance of the variable capacitor 56 is explained next with reference to FIG. 10. First, the acceleration determining unit 66 detects acceleration generated by a move and a change of a posture of the subject 1 (step S401), and determines whether the detected acceleration exceeds a predetermined threshold value (step S402). When it is determined that the detected acceleration does not exceed the predetermined threshold value, the process returns to step S401, and the acceleration determining unit 66 repeats the operation at steps S401 and S402.

When it is determined at step S402 that the detected acceleration exceeds the predetermined threshold value, the transmitting level determining unit 25 detects strength of a transmitted radio signal, as in the second embodiment (step S403), and determines whether the strength of a radio signal reaches an optimum value (step S404). When it is determined that the strength of a radio signal does not reach the optimum value, the transmitting level determining unit 25 changes a capacitance of the variable capacitor 56 (step S405), and the process returns to step S403 again. When it is determined that the strength of a radio signal reaches the optimum value, the transmitting level determining unit 25 fixes the capacitance of the variable capacitor 56 (step S406), and the process returns to step S401 again to repeat the above operation.

Based on the provision of the acceleration determining unit 66, a reduction of transmission efficiency can be suppressed when a shape and the like of the transmitting coil 24 provided in the transmitting/receiving jacket 65a change due to a move or a change of a posture of the subject 1. In other words, in the modified example, when the self inductance changes following a change in a shape and the like of the transmitting coil 24 due to a move or a change of a posture of the subject 1, and when the resonance frequency of the receiving resonance circuit 63 varies, the transmitting level determining unit 25 and the capacitance controller 57 start operation each time the resonance frequency changes, and adjust the capacitance of the variable capacitor 56 until the transmission strength reaches the optimum value. With this arrangement, satisfactory transmission efficiency can be maintained during a period from when the capsule endoscope is inserted into the subject till the capsule endoscope is discharged to the outside of the body.

At step S402, a threshold value is provided as the determination standard, to avoid the adjustment of the capacitance when the move or the like of the subject 1 is minute and the shape of the transmitting coil 24 does not change. The threshold value can be determined based on shapes of the transmitting/receiving jacket 65a and the transmitting coil 24, or can be set for each subject 1.

While the present invention has been explained above with reference to the first embodiment, the second embodiment, and the modified example, the present invention is not limited to the above. Those skilled in the art can conceive various embodiments, modifications, and application examples. For example, the acceleration determining unit 66 shown in the modified example can be added to the configuration of the first embodiment.

In the first embodiment, the second embodiment, and the modified example, the radio signal transmitted from the transmitting and receiving apparatus to the capsule endoscope includes the power supply signal and the control information signal. Alternatively, the radio signal can include one of the power supply signal and the control information signal, or can include a signal other than these signals. In other words, in the present invention, a reduction of one or both of transmission efficiency and reception efficiency can be suppressed with respect to the radio signal, regardless of the type of the radio signal.

In the first embodiment, the second embodiment, and the modified example, the capsule endoscope includes the LED, the CCD, and the like to image the inside of the subject 1. However, the body-insertable apparatus inserted into the subject is not limited to have this configuration, and can have a configuration that acquires other body information such as temperature information and pH information.

Third Embodiment

Figure 11:
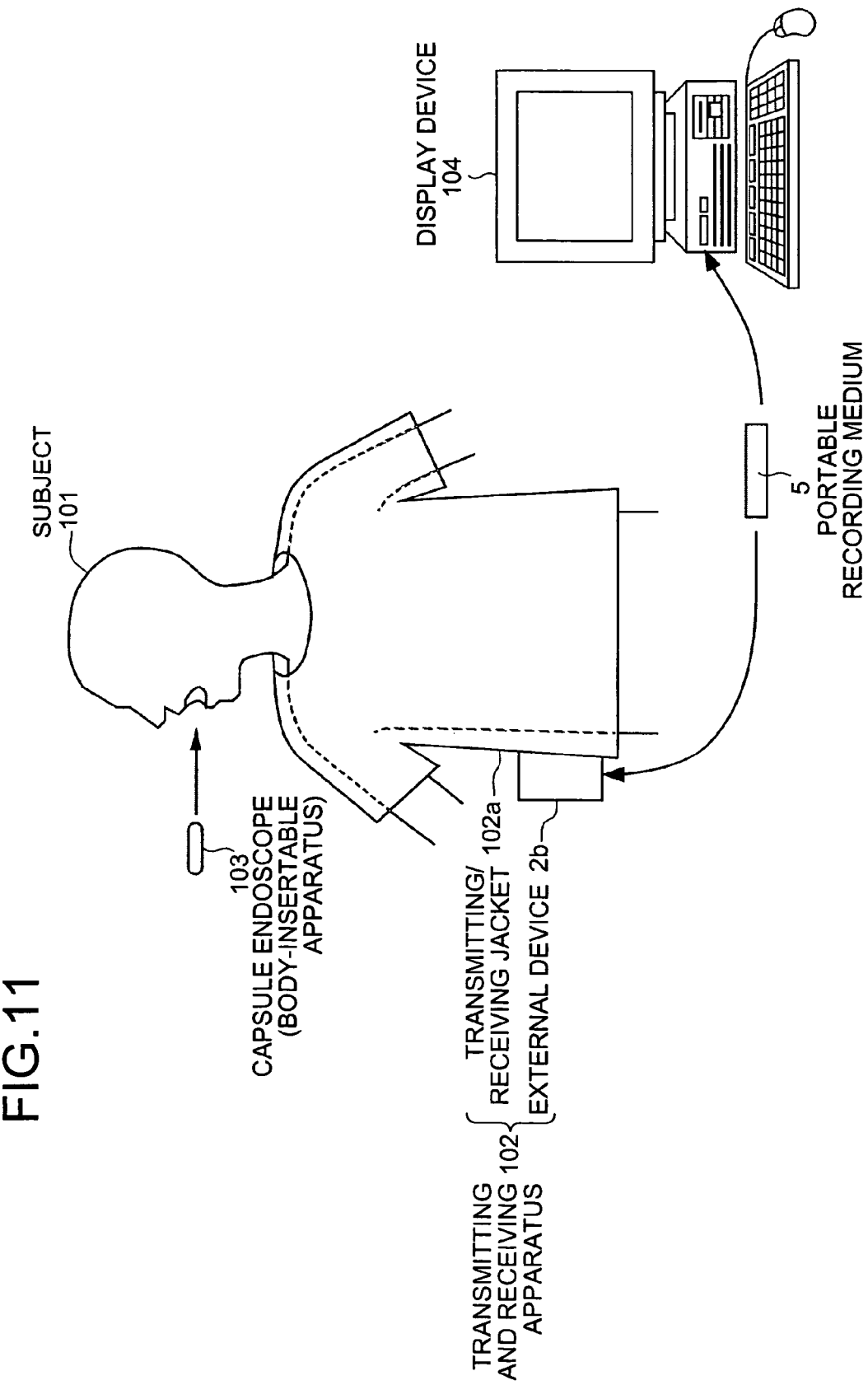
FIG. 11 is a schematic diagram showing an overall configuration of a radio intra-subject information acquiring system according to a third embodiment.

A radio intra-subject information acquiring system according to a third embodiment is explained next. FIG. 11 is a schematic diagram showing an overall configuration of the radio intra-subject information acquiring system according to the third embodiment. As shown in FIG. 11, the radio intra-subject information acquiring system includes a transmitting and receiving apparatus 102 that has a radio transmitting and receiving function, and a capsule endoscope 103 that is inserted into the body of a subject 101, operates based on driving power acquired from a radio signal transmitted from the transmitting and receiving apparatus 102, and transmits data to the transmitting and receiving apparatus 102 by imaging the body cavity. The radio intra-subject information acquiring system also includes a display device 104 that displays body-cavity images based on data received by the transmitting and receiving apparatus 102, and a portable recording medium 105 that delivers data between the transmitting and receiving apparatus 102 and the display device 104. The transmitting and receiving apparatus 102 also includes a transmitting/receiving jacket 102a that the subject 101 wears, and an external device 102b that processes a radio signal transmitted and received via the transmitting/receiving jacket 102a.

The display device 104 displays a body-cavity image picked up by the capsule endoscope 103, and has a configuration of a workstation or the like that displays images based on data acquired by the portable recording medium 105. Specifically, the display device 104 can have a configuration that directly displays images with a CRT display, a liquid crystal display or the like, or can be configured to output images to other medium as in a printer.

The portable recording medium 105 is attachable to and detachable from the external device 102b and the display device 104, and can output or record information when the portable recording medium 105 is mounted on either of the two. Specifically, during a period while the capsule endoscope 103 is moving within the body cavity of the subject 101, the portable recording medium 105 is mounted on the external device 102b and records data transmitted from the capsule endoscope 103. After the capsule endoscope 103 is discharged from the subject 101, that is, after the capsule endoscope 103 has ended imaging the inside of the subject 101, the portable recording medium 105 is removed from the external device 102b and is mounted on the display device 104 so that the display device 104 reads out the recorded data. When the portable recording medium 105 such as a Compact Flash (Registered Trademark) memory delivers data between the external device 102b and the display device 104, the subject 101 can move freely during a period while the capsule endoscope images the body cavity, unlike when the external device 102b is connected to the display device 104 via a cable.

Figure 12:
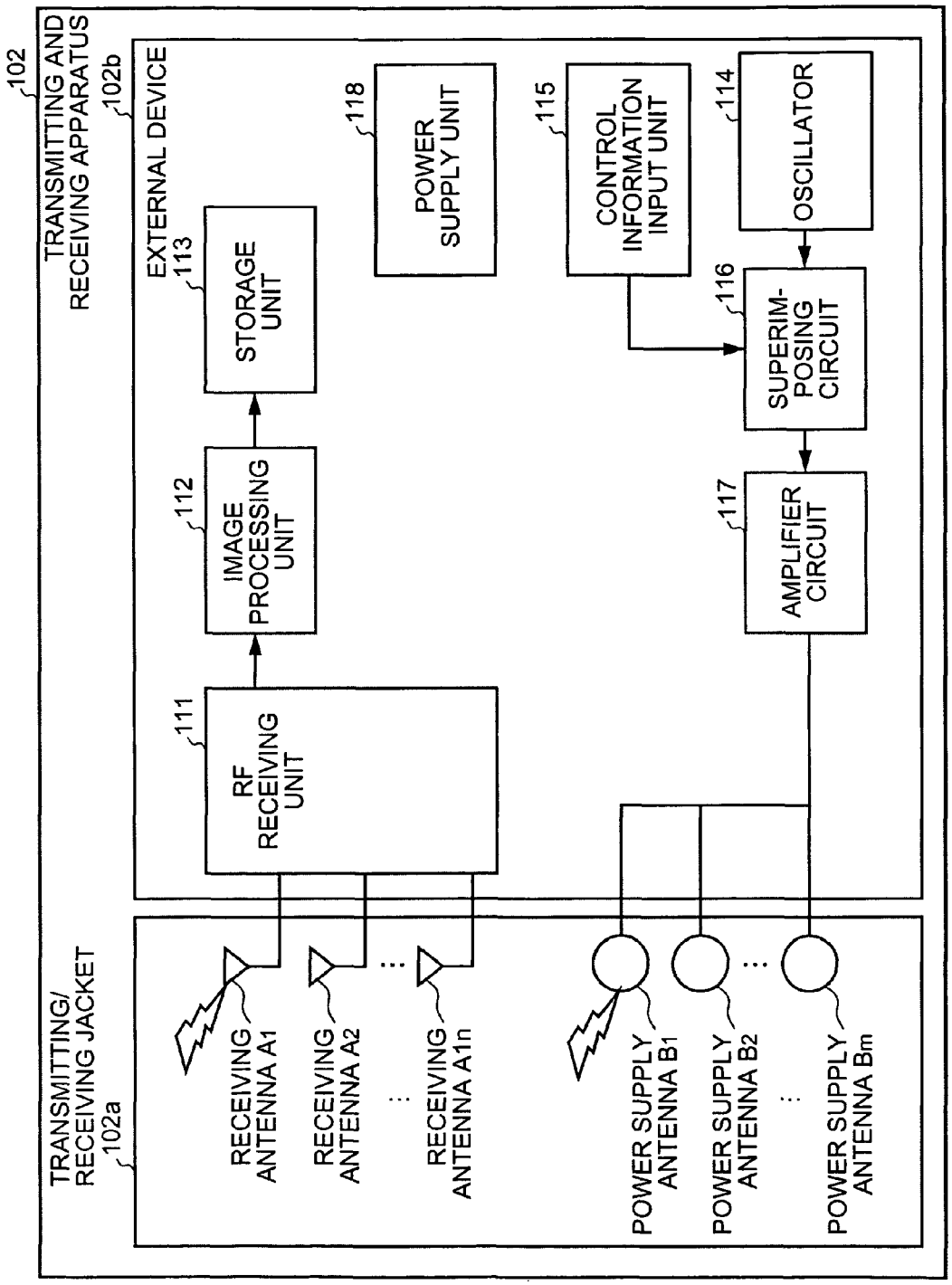
FIG. 12 is a block diagram schematically showing a configuration of a transmitting and receiving apparatus that constitutes a radio intra-subject information acquiring system.

The transmitting and receiving apparatus 102 has a function of a power supply apparatus that transmits power to the capsule endoscope 103, and has a function of a receiving apparatus that receives body-cavity image data transmitted from the capsule endoscope 103. FIG. 12 is a block diagram schematically showing a configuration of the transmitting and receiving apparatus 102. As shown in FIG. 12, the transmitting and receiving apparatus 102 includes a transmitting jacket 102a having a shape that the subject 101 can wear and having receiving antennas A1 to An and power supply antennas B1 to Bm, and an external device 102b that processes a radio signal transmitted and received.

The external device 102b has a function of processing a radio signal transmitted from the capsule endoscope 103. Specifically, as shown in FIG. 12, the external device 102b includes: an RF receiving unit 111 that executes a predetermined process to radio signals received by the receiving antennas A1 to An, extracts image data acquired by the capsule endoscope 103 from the radio signals, and outputs the extracted image data; an image processing unit 112 that executes necessary process to the output image data; and a storage unit 113 that records image-processed image data. The portable recording medium 105 records image data via the storage unit 113.

The external device 102b has a function of generating a radio signal to be transmitted to the capsule endoscope 103. Specifically, the external device 102b includes: an oscillator 114 that generates a power supply signal and prescribes an oscillation frequency; a control information input unit 115 that generates a control information signal to control a driving state of the capsule endoscope 103; a superimposing circuit 116 that combines a power supply signal with a control information signal; and an amplifier circuit 117 that amplifies strength of a combined signal. A signal amplified by the amplifier circuit 117 is transmitted to the power supply antennas B1 to Bm, and is transmitted to the capsule endoscope 103. The external device 102b includes a power supply unit 118 having a predetermined capacitor or an AC power source adaptor. Constituent elements of the external device 102b use power supplied from the power supply unit 118 as driving energy.

Figure 13:
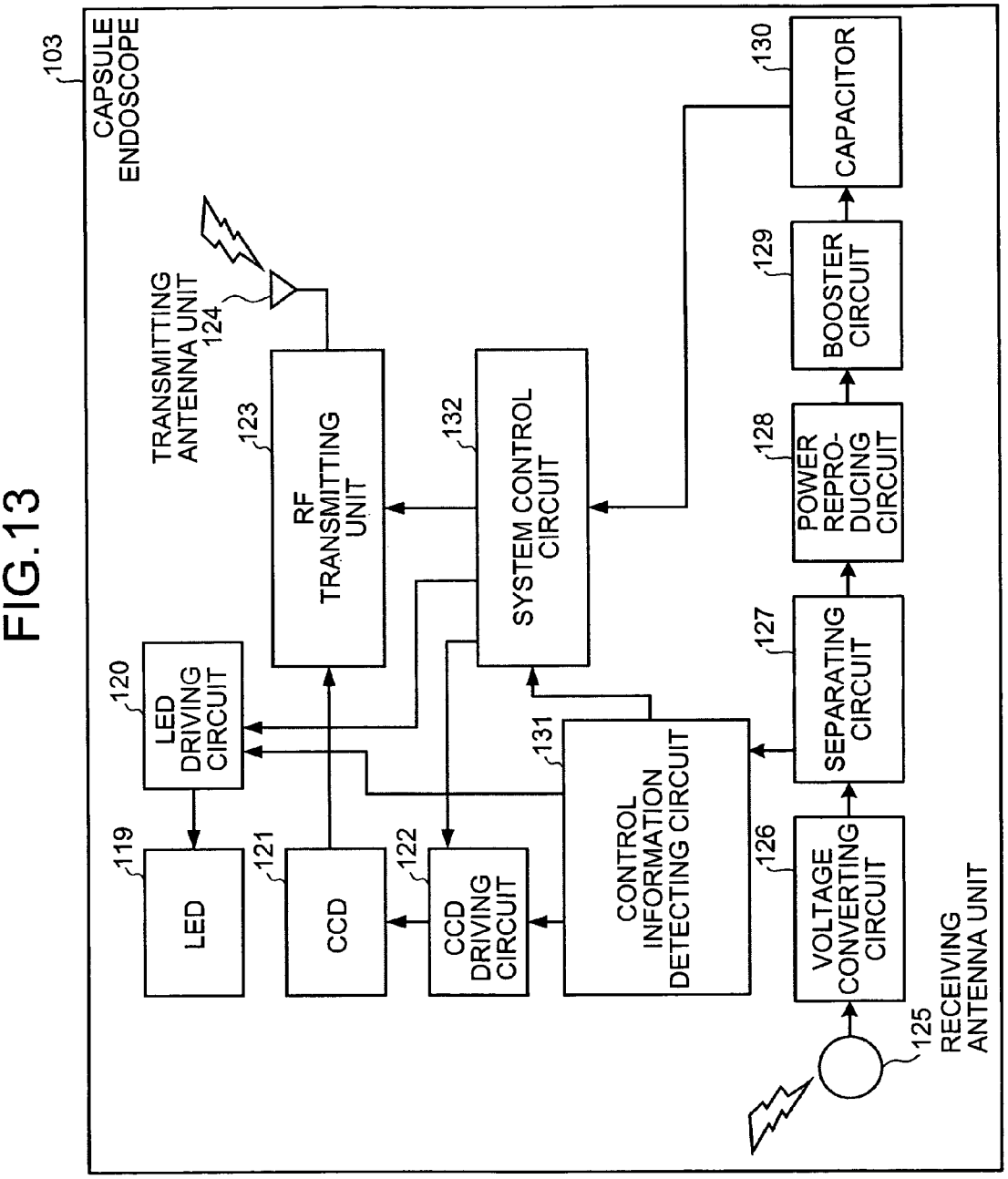
FIG. 13 is a block diagram schematically showing a configuration of a capsule endoscope that constitutes a radio intra-subject information acquiring system.

The capsule endoscope 103 that functions as one example of the body-insertable apparatus is explained next. FIG. 13 is a block diagram schematically showing a configuration of the capsule endoscope 103. As shown in FIG. 13, the capsule endoscope 103 includes: an LED 119 that illuminates an imaging area at the time of imaging of the inside of the subject 101; an LED driving circuit 120 that controls the driving state of the LED 119; and a CCD 121 that images an area illuminated by the LED 119. The capsule endoscope 103 also includes: a CCD driving circuit 122 that controls the driving state of the CCD 121; an RF transmitting unit 123 that modulates image data acquired by imaging by the CCD 121, and generates an RF signal; a transmitting antenna unit 124 that transmits an RF signal output from the RF transmitting unit 123; and a system control circuit 132 that controls the operation of the LED driving circuit 120, the CCD driving circuit 122, and the RF transmitting unit 123.

Based on the provision of these mechanisms, the CCD 121 acquires image information of an examined area illuminated by the LED 119, while the capsule endoscope 103 is inserted in the subject 101. The RF transmitting unit 123 converts the acquired image information into an RF signal, and transmits the RF signal to the outside via the transmitting antenna unit 124.

The capsule endoscope 103 also includes: a receiving antenna unit 125 that receives a radio signal transmitted from the transmitting and receiving apparatus 102; a voltage converting circuit 126 that converts a voltage of a signal received by the receiving antenna unit 125; and a separating circuit 127 that separates a power supply signal from the voltage-converted signal. The capsule endoscope 103 also includes: a power reproducing circuit 128 that reproduces power from a separated power supply signal; and a capacitor 130 that stores power boosted by a booster circuit 129 that boosts reproduced power. The capsule endoscope 103 also includes a control information detecting circuit 131 that detects content of a control information signal from the component separated from the power supply signal by the separating circuit 127, and that outputs a control signal to the LED driving circuit 120, the CCD driving circuit 122, and the system control circuit 132 according to need.

Based on the provision of these mechanisms, in the capsule endoscope 103, the receiving antenna unit 125 first receives a radio signal transmitted from the transmitting and receiving apparatus 102, the voltage converting circuit 126 converts a voltage of the signal, and the separating circuit 127 separates a power supply signal and a control information signal from the radio signal. The control information signal is output to the LED driving circuit 120, the CCD driving circuit 122, and the system control circuit 132, via the control information detecting circuit 131, and is used to control the driving states of the LED 119, the CCD 121, and the RF transmitting unit 123. On the other hand, the power reproducing circuit 128 reproduces the power supply signal as power. The booster circuit 129 boosts the potential of the reproduced power to the potential of the capacitor 130, and stores the boosted power into the capacitor 130. The capacitor 130 supplies power to the constituent elements of the system control circuit 132 and others. As explained above, the capsule endoscope 103 is supplied with power from the transmitting and receiving apparatus 102 by radio transmission.

Figure 14:
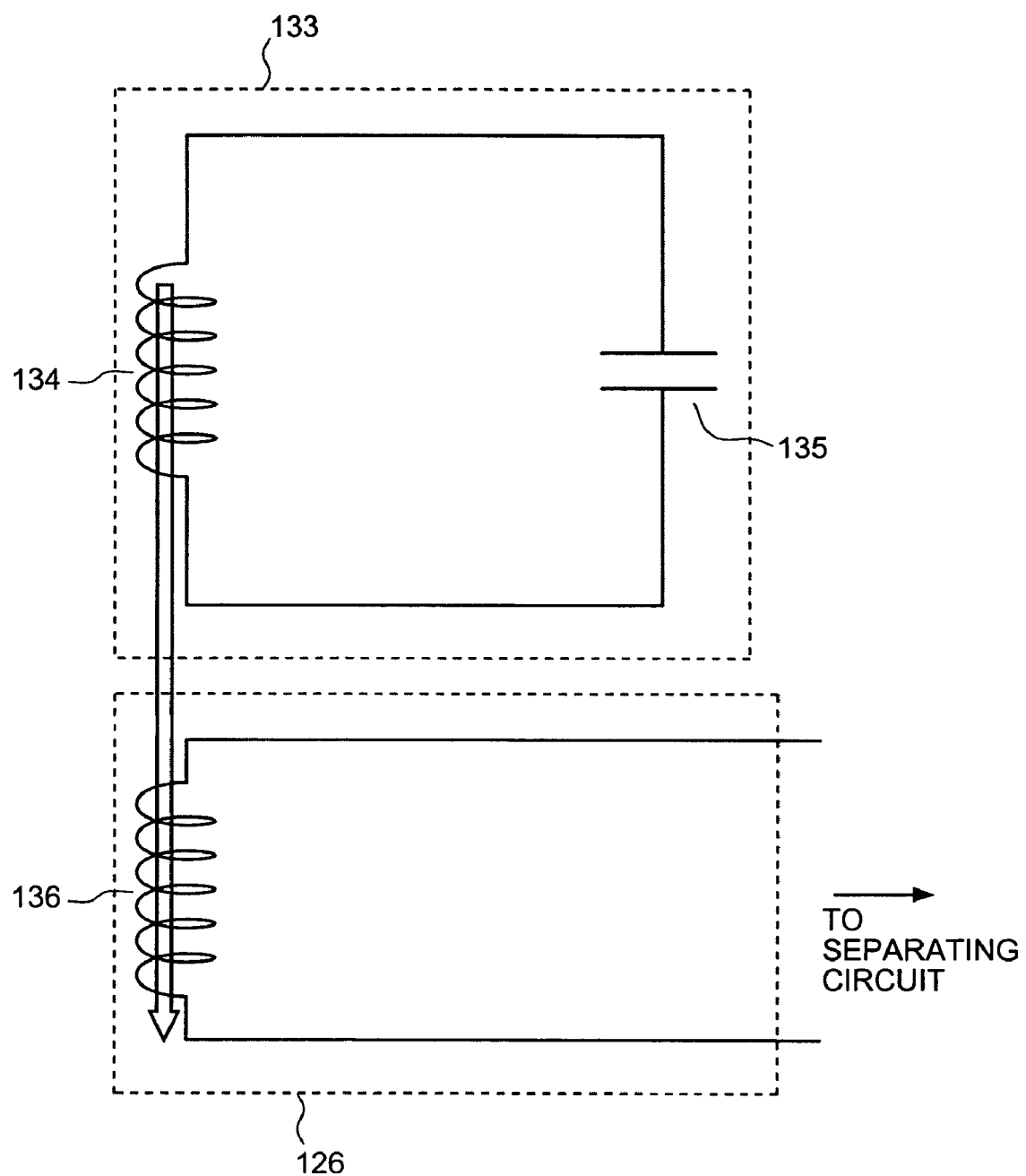
FIG. 14 is a circuit diagram showing a relationship between a receiving resonance circuit and a voltage converting circuit that constitute a capsule endoscope.

Configurations of the receiving antenna unit 125 and the voltage converting circuit 126 among the constituent elements of the capsule endoscope 103 are explained next. FIG. 14 is a circuit diagram showing a relationship between a receiving resonance circuit 133 and a voltage converting circuit 126 that constitute a receiving antenna unit 125. As shown in FIG. 14, the receiving resonance circuit 133 includes a receiving coil 134 and a receiving capacitor 135. The receiving resonance circuit 133 has a resonance frequency determined based on a self inductance value of the receiving coil 134 and an electrostatic capacitance of the receiving capacitor 135. Shapes of the receiving coil 134 and the receiving capacitor 135 are determined so that the resonance frequency becomes substantially equal to the frequency of the oscillator 114 provided in the transmitting and receiving apparatus 102.

On the other hand, the voltage converting circuit 126 includes a power supply coil 136 disposed near the receiving coil 134, and induced electromotive force appears in a power supply coil 136 based on a magnetic field generated in the receiving coil 134 at the time of receiving a radio signal. The power supply coil 136 has a smaller number of winding than that of the receiving coil 134 for the reason described later.

Figure 15:
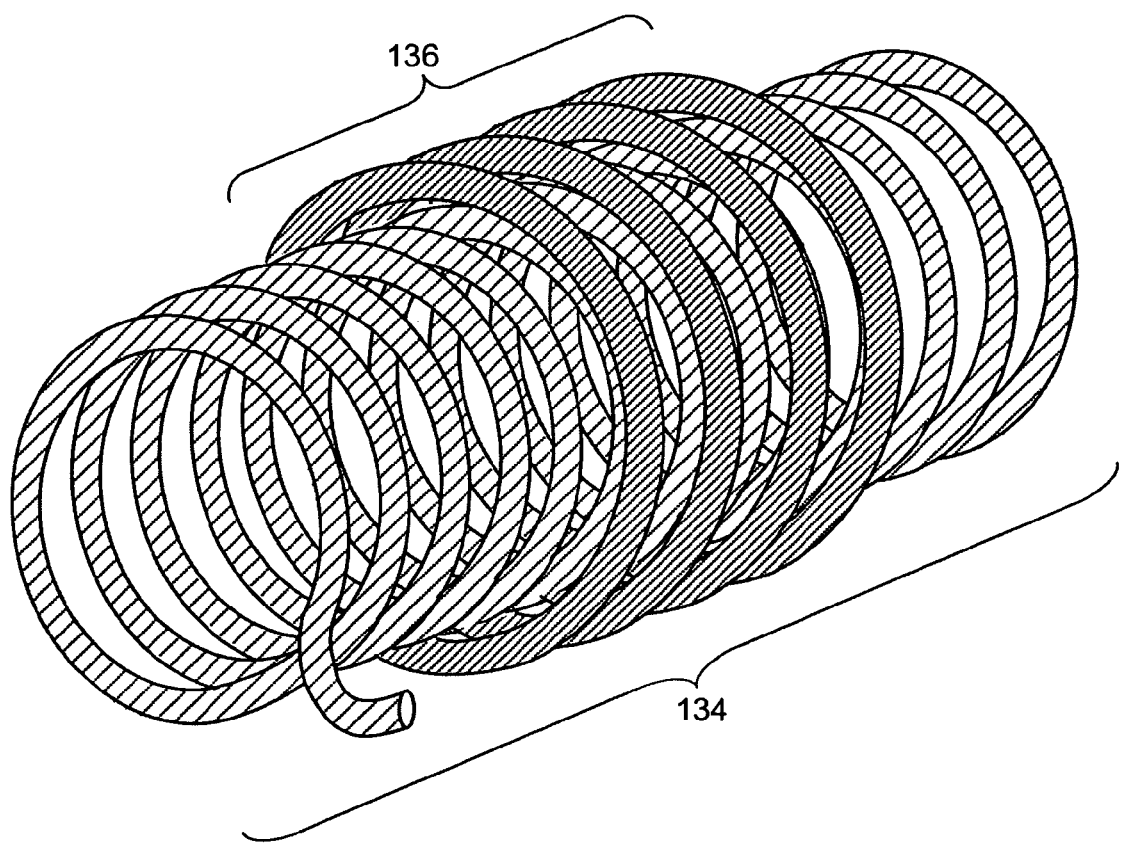
FIG. 15 shows a specific positional relationship between a receiving coil which constitutes a receiving resonance circuit and a power supply coil which constitutes a voltage converting circuit.
Figure 16:
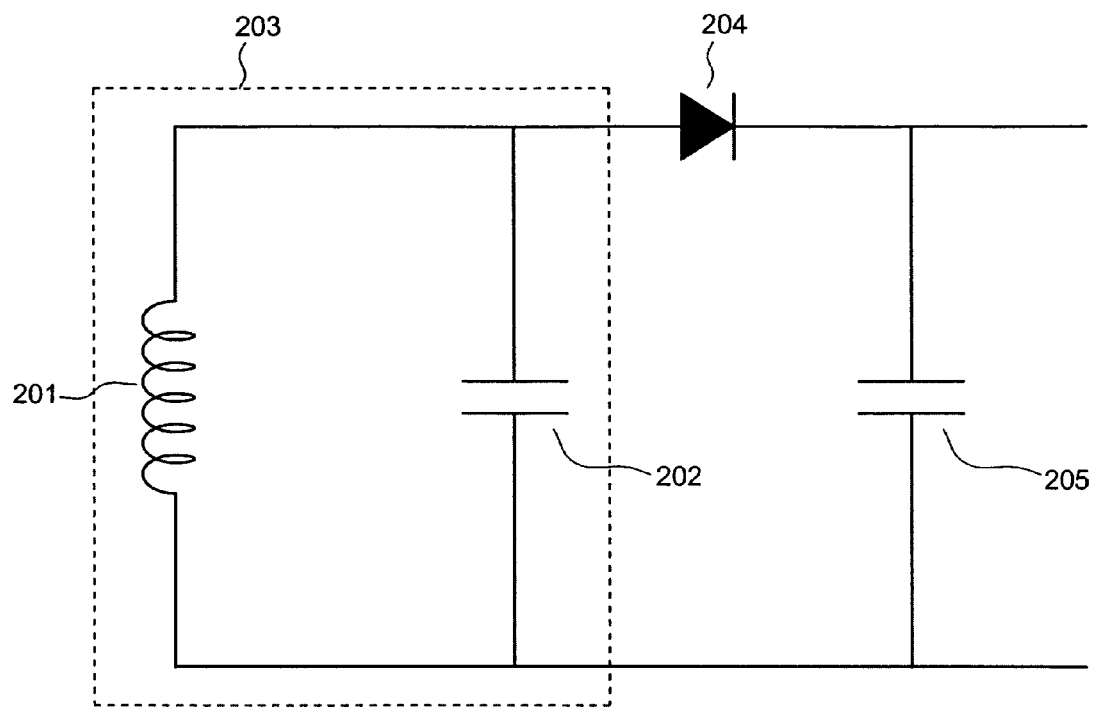
FIG. 16 is a circuit diagram schematically showing a configuration that extracts power by receiving a radio signal transmitted from the outside, in a capsule endoscope according to a conventional technique.
Figure 17:
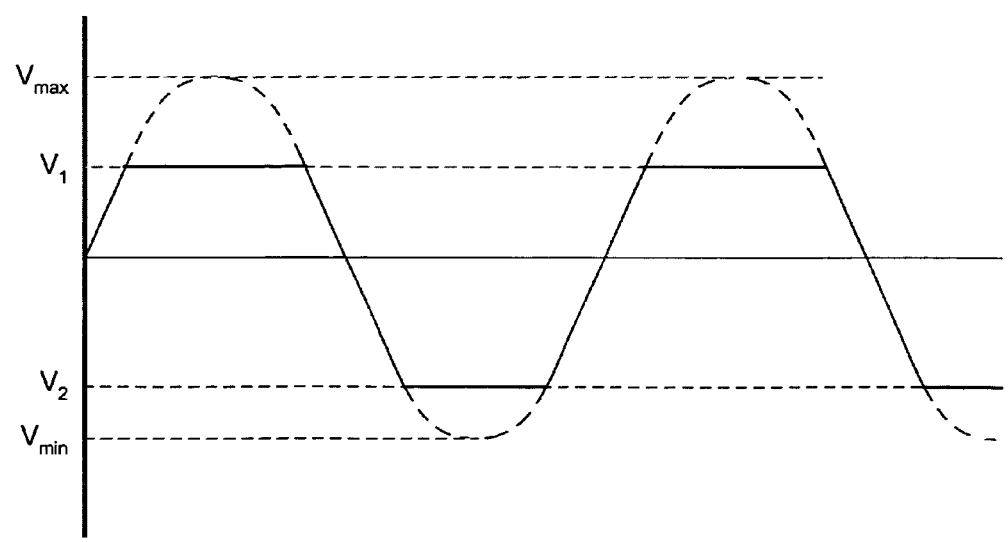
FIG. 17 is a schematic graph showing a voltage waveform of a received power signal, in a capsule endoscope according to a conventional technique.

A detailed configuration of the receiving coil 134 and the power supply coil 136 is explained. FIG. 15 is a schematic diagram showing a detailed configuration of the receiving coil 134 and the power supply coil 136. As shown in FIG. 15, at least the internal periphery of the power supply coil 136 is brought into contact with the external periphery of the receiving coil 134 having a configuration similar to that of the conventional coil. More preferably, the power supply coil 136 is closely wound around the receiving coil 134. The receiving coil 134 and the power supply coil 136 are configured by, for example, insulation-coated copper lines, and are mutually electrically insulated. Based on this positional relationship, a large part of a magnetic field generated by the receiving coil 134 passes through the power supply coil 136.

The operation of the voltage converting circuit 126 is explained next. The receiving resonance circuit 133 has a resonance frequency substantially equal to the frequency of a radio signal transmitted from the transmitting and receiving apparatus 102. The resonance frequency resonates with the radio signal during the reception time, and current flows within the circuit. A magnetic field corresponding to the radio signal is generated in a direction of an arrowhead shown in FIG. 14 in the receiving coil 134, according to a change of the current flowing within the receiving resonance circuit 133 during the reception.

The magnetic field generated in the receiving coil 134 reaches the power supply coil 136 provided near the receiving coil 134, and the power supply coil 136 generates induced electromotive force based on a change in the strength of the magnetic field. The induced electromotive force generated in the power supply coil 136 becomes smaller than a voltage generated in the receiving coil 134, based on a size relationship of the number of windings of coils. A predetermined current flows through the power supply coil 136 corresponding to this induced electromotive force. Power is reproduced based on the current and the induced electromotive force, and the reproduced power is stored into the capacitor 130. The capsule endoscope 103 operates to exert a predetermined function such as imaging, using the power stored in the capacitor 130.

Advantages of the radio intra-subject information acquiring system according to the third embodiment is explained next. First, because the radio intra-subject information acquiring system according to the third embodiment includes the voltage converting circuit 126, there is an advantage that high-strength power can be supplied via a radio transmission.

As explained above, because the capsule endoscope 103 is swallowed by the subject 101 and moves within the subject 101, the capsule endoscope 103 needs to be made compact to decrease load given to the subject 101, and the receiving coil 134 that configures the receiving antenna unit 125 also needs to be made compact. Therefore, when current is directly extracted from the receiving resonance circuit 133, the output voltage is saturated along the increase in the strength of transmitted power, and there is a possibility that a part of the transmitted radio signal cannot be taken out.

Therefore, in the third embodiment, the capsule endoscope 103 has the voltage converting circuit 126 that decreases the voltage of the electric signal generated in the receiving resonance circuit 133, separately from the receiving antenna unit 125 that includes the receiving resonance circuit 133 to resonate with the transmitted radio signal. The inventors have confirmed that when the voltage of the electric signal received by the voltage converting circuit 126 is output to the separating circuit 127 after the voltage is converted, the voltage is not easily saturated as compared with when the voltage is directly extracted from the receiving resonance circuit 133. What kind of mechanism avoids the occurrence of voltage saturation is not necessarily clear at present. It is considered that probably power is extracted from the voltage converting circuit 126 that includes a circuit configuration different from the resonance circuit.

From the above, the radio intra-subject information acquiring system according to the third embodiment has an advantage in that, by using the voltage converting circuit 126, the occurrence of saturation in the strength of the extracted power can be suppressed regardless of the strength of the transmitted radio signal. In other words, the capsule endoscope 103 according to the third embodiment can acquire driving power corresponding to the strength of the radio signal transmitted from the transmitting and receiving apparatus 102, and the radio intra-subject information acquiring system according to the third embodiment can supply high-strength power by radio transmission.

The radio intra-subject information acquiring system according to the third embodiment also has an advantage of being able to suppress a reduction in the voltage following a voltage conversion, by providing the power supply coil 136 shown in FIG. 15. As shown in FIG. 15, the power supply coil 136 has its internal periphery disposed on the external periphery of the receiving coil 134, and a magnetic field formed by the receiving coil during a reception of a radio signal passes through the power supply coil 136 without a leakage. Therefore, the magnetic field generated by the receiving coil 134 can be used without a leakage due to the electromagnetic inductance in the power supply coil 136. Consequently, voltage conversion can be carried out while suppressing a power reduction.

Because the power supply coil 136 has the configuration shown in FIG. 15, there is an advantage that power can be transferred highly efficiently, without increasing the size of the capsule endoscope 103. In other words, instead of individually separately disposing the receiving coil 134 and the power supply coil 136, the power supply coil 136 has its internal periphery disposed on the external periphery of the receiving coil 134, thereby sharing a large part of the coil inside. Therefore, regardless of the additional provision of the power supply coil 136 to improve the power utilization efficiency, the area occupied by the coil inside the capsule endoscope 103 does not increase, and the capsule endoscope 103 having a size substantially the same as the size of the conventional capsule endoscope can be achieved. Either the whole or a part of the constituent elements of the capsule endoscope 103 such as the LED 119 and CCD 121 can be disposed in the internal space of the receiving coil 134 having the configuration shown in FIG. 15. When this configuration is provided, the capsule endoscope 103 can be made more compact.

While the present invention has been explained above with reference to the third embodiment, the present invention is not limited to the above. Those skilled in the art can conceive various embodiments, modifications, and application examples. For example, in the third embodiment, the capsule endoscope includes the LED, the CCD and the like to pick up images inside the subject 101. However, the body-insertable apparatus that is inserted into the subject is not limited to have this configuration, and can have a configuration that acquires other intra-subject information such as temperature information and pH information. The body-insertable apparatus can have an oscillator, and an ultrasonic image within the subject 101 can be acquired. Further, a plurality of pieces of information can be acquired from the intra-subject information.

While the radio signal transmitted from the transmitting and receiving apparatus to the capsule endoscope includes a power supply signal and a control information signal, the radio signal can include only the power supply signal, or can include other signals. In other words, when the transmitting and receiving apparatus performs radio-transmission of the power supply signal to be converted into power to the capsule endoscope 103, the present invention can be applied to this configuration.

In the third embodiment, the transmitting and receiving apparatus 102 includes the transmitting/receiving jacket 102a, and the transmitting/receiving jacket 102a includes the receiving antennas A1 to An and the power supply antennas B1 to Bm. Alternatively, the receiving antenna and the power supply antenna can be disposed at other position. Further, instead of the arrangement that the portable recording medium 104 transfers data between the transmitting and receiving apparatus 102 and the display device 104, the transmitting and receiving apparatus 102 and the display device 104 can be connected by wire or by radio.

The configuration of the voltage converting circuit 126 is not necessarily limited to the configurations shown in FIG. 14 and FIG. 15. The configurations shown in FIG. 14 and FIG. 15 show one example that suppresses a power reduction and suppresses the increase in the size of the capsule endoscope 103. The voltage converting circuit can have other configuration having a voltage converting function.

INDUSTRIAL APPLICABILITY

As described above, a radio intra-subject information acquiring system according to the present invention can be effectively applied to observations and diagnosis in the medical field, for example.

The invention claimed is:

1. A radio intra-subject information acquiring system comprising:
   a body-insertable apparatus that is inserted into a subject, the body-insertable apparatus including,
      a receiving resonance circuit formed with a variable capacitor and a receiving coil, and
      a capacitance controller that changes a capacitance of the variable capacitor so as to decrease a frequency difference between a resonance frequency of the receiving resonance circuit and a frequency of a radio signal received; and
   a transmitting and receiving apparatus that is disposed at the outside of the subject, and performs radio communications with the body-insertable apparatus, the transmitting and receiving apparatus including,
      a frequency variable oscillator that prescribes an oscillation frequency of a transmitted radio signal, and can adjust the oscillation frequency,
      a transmitting resonance circuit formed with a fixed capacitor and a transmitting coil, and
      a frequency controller that controls the frequency variable oscillator so as to decrease a frequency difference between the oscillation frequency and a resonance frequency of the transmitting resonance circuit that changes according to a change in a self inductance value of the transmitting coil.

2. The radio intra-subject information acquiring system according to claim 1, wherein
   the transmitting and receiving apparatus further includes a transmitting level determining unit that determines strength of a radio signal transmitted by the transmitting resonance circuit, and
   the frequency controller changes the frequency while referencing the strength of the radio signal determined by the transmitting level determining unit.

3. The radio intra-subject information acquiring system according to claim 1, wherein
   the body-insertable apparatus further includes a receiving level determining unit that determines strength of a radio signal received by the receiving resonance circuit, and
   the capacitance controller changes a capacitance of the variable capacitor while referencing the strength of the radio signal determined by the receiving level determining unit.

4. The radio intra-subject information acquiring system according to claim 3, wherein the capacitance controller changes a capacitance of the variable capacitor so that strength of the radio signal becomes equal to or smaller than a permissible level.

5. The radio intra-subject information acquiring system according to claim 1, further comprising a wearing member that the subject wears at the time the body-insertable apparatus is inserted into the subject, wherein the transmitting coil is disposed on the wearing member.

6. The radio intra-subject information acquiring system according to claim 5, wherein the transmitting coil is formed to wrap around the subject when the subject wears the wearing member.

7. The radio intra-subject information acquiring system according to claim 1, wherein the variable capacitor is formed with a variable capacitance diode.

8. The radio intra-subject information acquiring system according to claim 1, wherein
   the variable capacitor is formed with plural mechanisms connected in parallel, each mechanism including a fixed capacitor and a switching unit connected with each other, and a capacitance changes when the switching unit is turned on and off.

9. The radio intra-subject information acquiring system according to claim 1, wherein
   the transmitting and receiving apparatus transmits a radio signal including at least a power supply signal which is to be converted into driving power inside the body-insertable apparatus to the body-insertable apparatus.

10. The radio intra-subject information acquiring system according to claim 1, wherein the frequency controller changes the frequency according to a predetermined algorithm.

* * * * *